(12) United States Patent
Berneth et al.

(10) Patent No.: US 6,600,589 B1
(45) Date of Patent: Jul. 29, 2003

(54) ELECTROCHROMIC DEVICE WITH A YELLOW FILTER

(75) Inventors: Horst Berneth, Leverkusen (DE); Stephan Michaelis, Odenthal (DE); Ralf Neigl, Yorktown Heights, NY (US); Hermann Jens Womelsdorf, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/786,515

(22) PCT Filed: Aug. 26, 1999

(86) PCT No.: PCT/EP99/06260
§ 371 (c)(1),
(2), (4) Date: Mar. 5, 2001

(87) PCT Pub. No.: WO00/14172
PCT Pub. Date: Mar. 16, 2000

(30) Foreign Application Priority Data

Sep. 8, 1998 (DE) .......................................... 198 40 938
May 4, 1999 (DE) .......................................... 199 20 360

(51) Int. Cl.⁷ ........................... G02F 1/15; B32B 17/06; C07D 241/46
(52) U.S. Cl. ........................ 359/265; 359/275; 428/583; 428/426; 514/334; 544/347; 546/257
(58) Field of Search ................................. 359/265, 273, 359/275, 267; 514/332, 334, 336, 344; 544/347; 546/257; 252/583, 600; 428/583, 426

(56) References Cited

U.S. PATENT DOCUMENTS

| | | | |
|---|---|---|---|
| 3,280,701 A | 10/1966 | Donnelly et al. | 359/267 |
| 4,902,108 A | 2/1990 | Byker | 359/265 |

(List continued on next page.)

FOREIGN PATENT DOCUMENTS

| | | |
|---|---|---|
| DE | 39 17 323 | 11/1990 |
| DE | 44 35 211 | 4/1995 |
| WO | 94/23333 | 10/1994 |
| WO | 98/05737 | 2/1998 |
| WO | 98/35267 | 8/1998 |
| WO | 99/09112 | 2/1999 |

OTHER PUBLICATIONS

*Database WPI, Section Ch, Week 199008, Derwent Publications Ltd., London, GB; Class E13, AN 1990–054976, XP002123138, & JP 02 008286, A (Tomoegawa Paper Mfg Co Ltd), Jan. 11, 1990, Zusammenfassung.

(List continued on next page.)

*Primary Examiner*—Loha Ben
(74) *Attorney, Agent, or Firm*—Godfried R. Akorli; Diderico van Eyl

(57) ABSTRACT

The invention relates to a light-protected electrochromic device containing a pair of glass or plastic sheets or plastic films. One side of at least one of said sheets or films, preferably both sheets or films, is provided with an electroconductive coating. At least one of said sheets or films and its electroconductive coating are transparent and the other can be metallized. The electroconductive coating of at least one of the two sheets or films can be divided up into separate, individually contacted surface segments. The sheets or films are joined by a sealing ring on the sides of their electroconductive coatings and the volume created by the sheets or films and the sealing ring is filled with an electrochromic medium. The invention is characterized in that the electrochromic device contains a yellow filter for which the wavelength at which absorbance in the long-wave flank reaches half of the very long-wave maximum absorbance value is between 370 and 500 nm, preferably between 380 and 470 nm. The invention is characterized by a considerably improved resistance to light in its activated state.

14 Claims, 1 Drawing Sheet

U.S. PATENT DOCUMENTS

Figure 1:
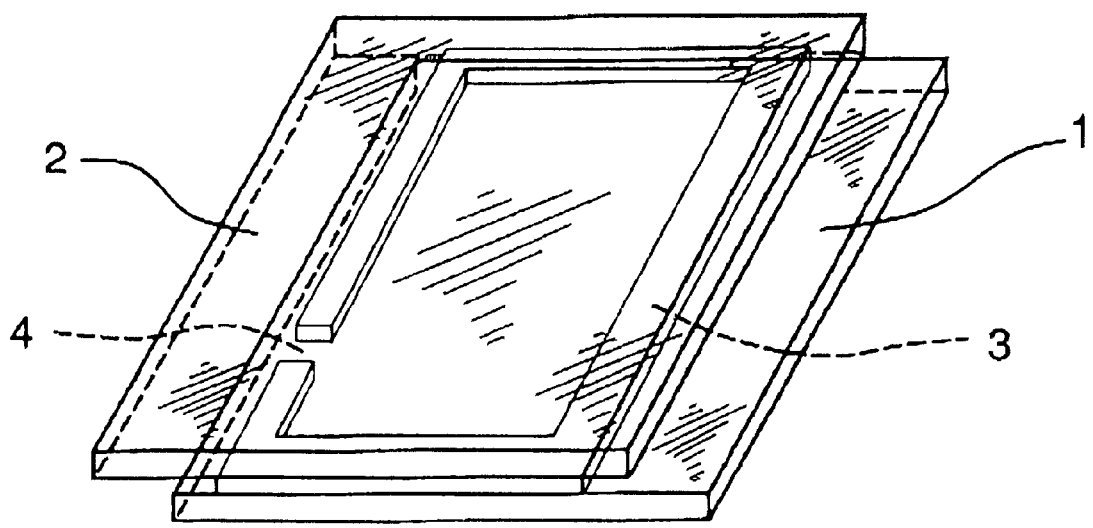

| | | | |
|---|---|---|---|
| 5,073,012 A | 12/1991 | Lynam | 359/265 |
| 5,128,267 A | 7/1992 | Köcher et al. | 436/92 |
| 5,140,455 A | 8/1992 | Varaprasad et al. | 359/275 |
| 5,151,816 A | 9/1992 | Varaprasad et al. | 359/275 |
| 5,239,405 A | 8/1993 | Varaprasad et al. | 359/272 |
| 5,278,693 A | 1/1994 | Theiste et al. | 359/272 |
| 5,280,380 A | 1/1994 | Byker | 359/265 |
| 5,300,637 A | 4/1994 | Hatch et al. | 548/162 |
| 5,322,680 A | 6/1994 | Beck et al. | 436/73 |
| 5,472,477 A | 12/1995 | König | 75/343 |
| 5,553,630 A | 9/1996 | Dupuis et al. | 132/202 |
| 5,680,245 A | 10/1997 | Lynam | 359/265 |
| 5,747,012 A | 5/1998 | Dahms | 424/60 |
| 5,827,507 A | 10/1998 | Oshima et al. | 424/59 |
| 6,207,292 B1 | 3/2001 | Berneth et al. | 428/583 |

OTHER PUBLICATIONS

*Proceedings of the Spie, US, Spie, Bellingham, VA, Bd. 2531, Seite 60–69, XP000671702, das ganze Dokument, A. Hagfeld et al, "Nanostructured T102 Semiconductor Electrodes Modified With Surface Attached Viologens: Applications For Displays And Smart Windows".

Adv. Materials, 3 (month unavailable), 1991, pp. 225–236, S. Hünig et al, "DCNQIs–New Electron Acceptors For Charge–Transfer Complexes And Highly Conducting Radical Anion Salts".

J. Am. Chem. Soc., 99, (month unavailable), 1977, pp. 6120–6122, M. Horner et al "Bicyclo[1.1.0]Butanes. A New Synthetic Route and Valence Isomerizations".

J. Am. Chem. Soc., 117, (month unavailable), 1995, pp. 8528–8535, G. V. Tormos et al "Dithiadiazafulvalenes–New Strong Electron Donors, Synthesis, Isolation, Properties, And EPR Studies".

Angew Chem., 90, (month unavailable), 1978, pp. 927–938, Deuchert et al, Mehrstufige Organische Redoxesysteme–Ein Allgemeines Strukturprinzip.

Ullmann's Encyc. Of Ind. Chem., vol. 8, (month unavailable), 1987, pp. 622–623, 3.2.3 "Electrochemical Displays".

Translated from Elecktrokhimiya, (month unavailable), 1977, pp. 24–28, I. V. Shelepin et al, "Electrochromism Of Organic Compounds I. Electrochemcial And Spectral Properties Of A System Based On Methylviologen And 3–Ethyl–2–Benzothiazolone Azine".

Translated From Elektrokhimiya, (month unavailable), 1978, pp. 271–274, O. A. Ushakov, et al, "Electrochromism Of Organic Compounds, Some Properties of Two–Electrode Cells".

Translated from Elektrokhimiya, (month unavailable), 1978, pp. 404–408,O. S. Abramzon et al, "Moisture–Exchange Processes in Hydrogen–Oxygen Cells with Capillary Membrane, III. Nonstationary Processes During Load Connection".

Topic in Current Chemistry, vol. 93, (month unavailable), 1980, pp. 1–44, A. Knop et al, "Chemsitry And Application of Phenolic Resins".

J. Org. Chem, 57, (month unavailable), 1992, pp. 1849–1855, G. A. Crispino et al, "Synthesis of Tripyridiniumylpropenyl Anions from Tripyridiniumylcyclopropanes and Cyclopropenes".

J. Chem. Soc., Perkin Trans., 2, (month unavailable), 1990, pp. 1777–1783, M. R. Bryce et al, "Synthesis And Redox Behaviour Of Highly Conjugated Bis(Benzo–1,3–dithiole) And Bis(Benzothiazole) Systems Containing Aromatic Linking Groups: Model Systems For Organic Metals".

ELECTROCHROMIC DEVICE WITH A YELLOW FILTER

The present invention relates to a light-stabilized electrochromic device and new electrochromic substances.

Electrochromic devices are already known, for example from D. Theis in Ullmann's Encyclopedia of Industrial Chemistry, Vol. A 8, p. 622, Verlag Chemie 1987 and WO-A 94/23333. A distinction is made between two basic types:

Type 1: full-area electrochromic device.

Type 2: electrochromic display devices having structured electrodes.

Type 1 is employed, for example, in electrically dimmable window panes or electrically dimmable automobile mirrors. Such devices are known, for example, from U.S. Pat. No. 4,902,108.

Type 2 is used in segmented and matrix displays. Such display devices have been proposed, for example, in DE-A 196 31 728. Such devices can be viewed in transmission or reflectively in the case of mirroring.

WO-A 94/23333 compares electrochromic materials of different constructions; however, these are not used as display devices:

Construction a: The electrochromic substances are fixed as a film or layer on the electrodes (Ullmann, see above).

Construction b: The electrochromic substances are deposited as a layer on the electrodes during the redox process (Ullmann, see above).

Construction c: The electrochromic substances remain permanently in solution.

For construction a), the best-known electrochromic material is the pair tungsten oxide/palladium hydride.

For construction b), viologens have been described as electrochromic substances. These devices are not self-extinguishing, so the image generated remains even after switching off the electric power and can only be extinguished again by reversing the polarity. Such devices are not particularly stable and do not allow a large number of switching cycles.

In addition, cells constructed using, in particular, tungsten oxide/palladium hydride cannot be operated using transmitted light because of the light scattering of these electrochromic layers, but can only be operated reflectively.

Elektrokhimiya 13, 32–37 (1977), 13, 404–408, 14, 319–322 (1978), U.S. Pat. Nos. 4,902,108 and 5,140,455 disclose an electrochromic system of this latter construction type c). In an electrochromic cell which is made up of conductively coated glass plates, a solution of a pair of electrochromic substances in an inert solvent is present.

As pair of electrochromic substances, use is made of one electrochemically reversibly reducible substance and one reversibly oxidizable substance. Each is colourless or only slightly coloured in the base state. Under the action of an electric potential, one substance is reduced and the other is oxidized, with both becoming coloured. After switching off the potential, both substances revert to the base state, with decolouration of lightening of colour occurring.

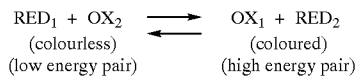

It is known from U.S. Pat. No. 4,902,108 that suitable pairs of redox substances are those whose reducible substance has at least two chemically reversible reduction waves in the cyclic voltammogram and the oxidizable substance correspondingly has at least two chemically reversible oxidation waves.

However, according to WO-A 94/23333, such solution systems of construction c) have serious disadvantages.

The diffusion of electrochromic substances in the solution results in diffuse colour boundaries and causes a high power consumption to maintain the coloured state, since the coloured substances are continually being converted back to the uncoloured state by recombination and reaction at the opposite electrode.

Nonetheless, various applications have been described for such electrochromic cells of construction c). For example, they can be configured as automobile rear view mirrors which, during night driving, can be darkened by application of an electrical potential and thus prevent dazzling by the headlights of vehicles behind (U.S. Pat. Nos. 3,280,701, 4,902,108, EP-A 0 435 689). Furthermore, such cells can also be used in windows or automobile sunroofs where they dim the sunlight after application of an electric potential. The use of such devices as electrochromic display devices, for example in segmented or matrix displays having structured electrodes, has likewise been described (DE-A 196 31 728).

The electrochromic cells normally comprise a pair of glass plates of which, in the case of an automobile mirror, one is mirrored. One side of these plates is coated with a light-transparent, electrically conductive layer, for example indium-tin oxide (ITO) where, in the case of display devices, this conductive coating is divided into electrically separate segments which are individually provided with contacts. A cell is built up from these plates by joining them via a sealing ring with their electrically conductive sides facing one another to form a cell. An electrochromic liquid is then introduced into the cell via an opening and the cell is tightly sealed. The two plates are connected to a power source via the ITO layers.

The above-described electrochromic devices are generally sensitive to light, in particular UV light. For this reason, U.S. Pat. No. 5,280,380, for example, describes electrochromic devices containing UV absorbers. Electrochromic automobile mirrors which contain such absorbers in an antisplinter coating have also been described (U.S. Pat. No. 5,073,012).

The UV protection known from the prior art effects an improvement in the light stability of the electrochromic devices in the unswitched, zero-current state. This is sufficient for use in automobile rear view mirrors since they are always unswitched during the day when the light is strong and are only switched, i.e. darkened, at night when there is little light.

For other applications of electrochromic devices, for example windows or display devices, this protection is not sufficient since it is precisely when the light is strong that they are switched.

It is an object of the present invention to improve the light stability of electrochromic devices in the switched state.

It has now surprisingly been found that protection of the electrochromic device in the wavelength region from 350 to 450 nm by means of a yellow filter considerably improves its light stability in the switched-on state.

The invention accordingly provides a light-stabilized electrochromic device comprising a pair of glass or plastic plates or plastic films of which at least one plate or film, preferably both plates or films, are provided on one side each with an electrically conductive coating, where at least one plate or film and its conductive coating is transparent, where the other can be mirrored and where the electrically conductive layer of at least one of the two plates or films can be divided into separate, individually contacted area segments, where the plates or films are joined via a sealing ring on the sides of their conductive coating and the volume formed by the two plates or films and the sealing ring is filled with an electrochromic medium, characterized in that the electrochromic device contains a yellow filter for which the wavelength at which the absorbance in the long-wavelength flank reaches half of the longest-wavelength maximum absorbance is in the range from 370 to 500 nm, preferably from 380 to 470 nm.

Particularly preferably, the wavelength at which the absorbance in the long-wavelength flank reaches half of the longest-wavelength maximum absorbance is in the range from 380 to 450 nm, very particularly preferably from 390 to 430 nm.

The absorption maximum is preferably in the range from 355 to 430 nm, particularly preferably from 360 to 410 nm, very particularly preferably from 370 to 405 nm. Very particular preference is given to substances and materials for which the width at half height of the absorption band, i.e. the width of the band at half its maximum absorbance, is less than 100 nm, in particular less than 80 nm, very particularly preferably less than 60 nm. The long-wavelength fall-off of the absorption band is preferably steeper than that on the short-wavelength side.

Preference is likewise given to materials which additionally filter out wavelengths below 350 nm. They then have, in the range from 370 to 450 nm, preferably from 380 to 420 nm, an absorption edge below which strong absorption takes place and above which weak or preferably no absorption takes place (edge filters). Such materials can be mixtures of individual materials whose individual absorptions are superimposed to produce this broad-band absorption having an edge at from 370 to 450 nm. They can, however, also be materials which have this property on their own. Examples are special glasses or oxidic or ceramic coatings and also, in particular, nanosize particles.

These yellow filters are present in the electrochromic medium and/or fixed on and/or in at least one of the two transparent plates or films. For example, the plates or films can be provided with transparent coatings in which these yellow filters are present. Such transparent coatings are, for example, plastics, e.g. polyurethanes, polyacrylates, polymethacrylates, polyamide, polycarbonate or polyester, or inorganic coatings, for example ones based on silicate, known as Ormocers.

The yellow filters thus have to be soluble or dispersible in the electrochromic medium or in the coating or in the plate or film so that no light scattering occurs. They can also be chemically bound in the coating or in the plate or film.

Suitable yellow filters are, in particular, yellow dyes which absorb at short wavelength.

Examples are:

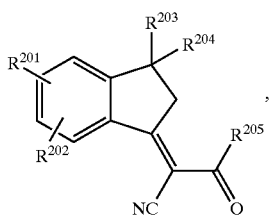
(CCI)

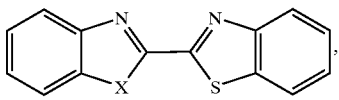
(CCII)

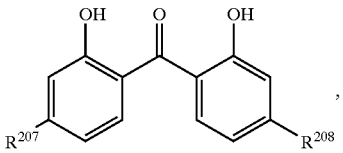
(CCIII)

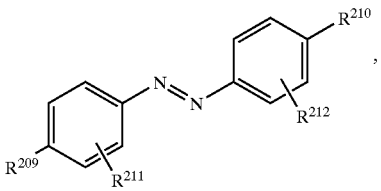
(CCIV)

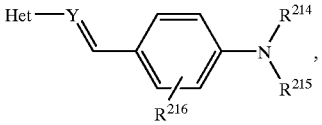
(CCV)

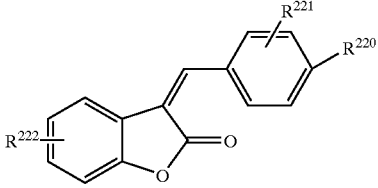
(CCVI)

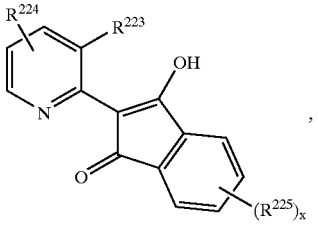
(CCVII)

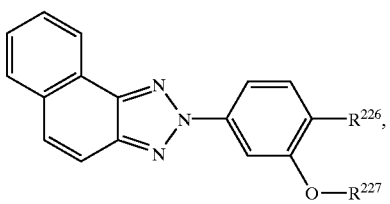
(CCVIII)

where
$R^{201}$ and $R^{202}$ represent, independently of one another, $C_1$–$C_8$-alkoxy,
$R^{203}$ and $R^{204}$ represent, independently of one another, hydrogen or $C_1$–$C_4$-alkyl,
$R^{205}$ represents $C_1$–$C_{18}$-alkyl or $C_1$–$C_{18}$-alkoxy,
X represents S or N—$R^{206}$,
$R^{206}$ and $R^{227}$ represent, independently of one another, $C_1$–$C_{12}$-alkyl,
$R^{207}$ and $R^{208}$ represent, independently of one another, hydroxy, $C_1$–$C_8$-alkoxy or $C_6$–$C_{10}$-aryloxy,
$R^{209}$ and $R^{210}$ represent, independently of one another, $C_1$–$C_8$-alkoxy, $C_1$–$C_8$-alkylthio, $NR^{217}R^{218}$, $C_6$–$C_{10}$-aryloxy, cyano, CO—$OR^{217}$, CO—$NR^{217}R^{218}$, $NR^{218}$—CO—$R^{219}$, $NR^{218}$—$SO_2$—$R^{219}$ and $R^{209}$ may also represent hydrogen or $C_1$–$C_4$-alkyl, $R^{211}$ and $R^{212}$ represent, independently of one another, hydrogen, halogen, $C_1$–$C_4$-alkyl, $C_1$–$C_4$-alkoxy or $NR^{218}$—CO—$R^{219}$, Het represents benzothiazol-2-yl, benzoxazol-2-yl, benzimidazol-2-yl, thiazol-2-yl, 1,3,4-thiadiazol-2-yl, 2- or 4-pyridyl, 2- or 4-quinolyl or 3,3-dimethylindolen-2-yl, which may each be substituted by methyl, methoxy, chloro, cyano, nitro, methoxycarbonyl, methylthio, dimethylamino, diethylamino or dipropylamino, Y represents N or C—$R^{213}$, $R^{213}$ represents hydrogen, $C_1$–$C_4$-alkyl, cyano, CO—$R^{219}$, CO—O—$R^{217}$ or CO—$NR^{217}R^{218}$, $R^{214}$ and $R^{215}$ represent, independently of one another, hydrogen, $C_1$–$C_8$-alkyl, CO—$R^{219}$ or $C_6$–$C_{10}$-aryl or $NR^{214}R^{215}$ represents pyrrolidino, piperidino or morpholino, $R^{216}$ represents hydrogen, halogen, $C_1$–$C_4$-alkyl, $C_1$–$C_4$-alkoxy or NH—CO—$R^{219}$, $R^{217}$ and $R^{218}$ represent, independently of one another, hydrogen, $C_1$–$C_8$-alkyl or $C_6$–$C_{10}$-aryl, $R^{219}$ represents $C_1$–$C_8$-alkyl or $C_6$–$C_{10}$-aryl, $R^{220}$ to $R^{222}$ represent, independently of one another, hydrogen, $C_1$–$C_8$-alkyl or $C_1$–$C_8$-alkoxy, $R^{223}$ represents hydrogen or hydroxy, $R^{224}$ represents hydrogen, halogen or $C_1$–$C_4$-alkyl, $R^{225}$ represents hydrogen or halogen, x represents an integer from 1 to 4 and $R^{226}$ represents CHO, CN, CO—$C_1$–$C_8$-alkyl or CO—$C_6$–$C_{10}$-aryl, where the alkyl, alkoxy and aryl radicals may bear further radicals such as alkyl, halogen, nitro, cyano, CO—$NH_2$, alkoxy or phenyl and the alkyl and alkoxy radicals can be linear or branched.

In particular, fluorescent dyes are also suitable as yellow filters.

Examples are:

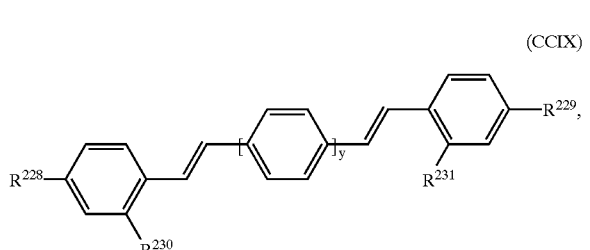
(CCIX)

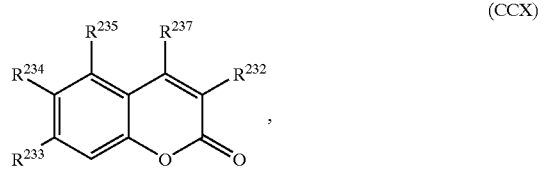
(CCX)

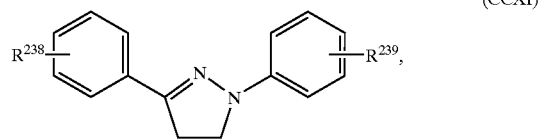
(CCXI)

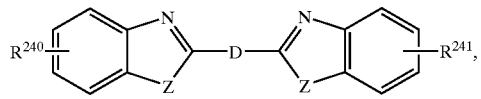
(CCXII)

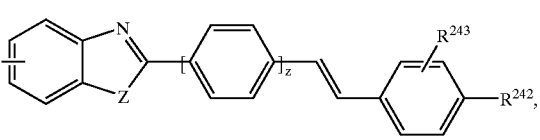
(CCXIII)

where $R^{228}$ to $R^{231}$ represent, independently of one another, hydrogen, halogen, cyano or $C_1$–$C_4$-alkoxy, y represents 1 or 2, $R^{232}$ represents hydrogen, cyano, CO—O—$C_1$–$C_4$-alkyl, $C_6$–$C_{10}$-aryl, thiophen-2-yl, pyrid-2- or -4-yl, pyrazol-1-yl or 1,2,4-triazol-1- or -4-yl, $R^{233}$ represents hydrogen, $C_1$–$C8$-alkoxy, 1,2,3-triazol-2-yl or di-$C_1$–$C_4$-alkylamino, $R^{234}$ and $R^{235}$ represent hydrogen or together represent a —CH=CH—CH=CH— bridge, $R^{237}$ represents hydrogen, $C_1$–$C_4$-alkyl or cyano, $R^{238}$ and $R^{239}$ represent, independently of one another, hydrogen, halogen, CO—$C_1$–$C_4$-alkyl or $SO_2$—$C_1$–$C_4$-alkyl, $R^{240}$, $R^{241}$ and $R^{243}$ represent, independently of one another, hydrogen or $C_1$–$C_8$-alkyl, Z represents O or N—$R^{244}$, D represents —CH=CH—, 1,4-phenylene, naphthalene-1,4-diyl, thiophene-2,5-diyl or furan-2,5-diyl, $R^{242}$ represents hydrogen, cyano or CO—O—$C_1$–$C_8$-alkyl, z represents 0 or 1 and $R^{244}$ represents $C^1$–$C_8$-alkyl, where the alkyl, alkoxy, aryl and heterocyclic radicals may bear further radicals such as alkyl, halogen, nitro, cyano, CO—$NH_2$, alkoxy or phenyl, the alkyl and alkoxy radicals can be linear or branched and the heterocyclic radicals can be benzo-fused.

The radicals $R^{201}$, $R^{205}$, $R^{206}$, $R^{207}$, $R^{209}$, $R^{211}$, $R^{214}$, $R^{220}$, $R^{227}$, $R^{233}$ and $R^{244}$ may also have the meaning —P—Q, where P is a bridging member and Q is a group which can be incorporated into a polymer. P is, for example, a —($CH_2$)p— group, where p is an integer from 1 to 12, and Q is, for example, OH (for polyesters, polyurethanes, polyureas), $NH_2$ (for polyureas or polyamides), —O—(CO)—CH=$CH_2$ or O—(CO)—C($CH_3$)=$CH_2$ for poly(meth)acrylates and copolymers with other olefinic monomers such as styrene, acrylonitrile, butadiene, etc.

The absorption maxima of the abovementioned compounds of the formulae (CCI) to (CCXIII) are, depending on the substituents, for example, in the following ranges:

(CCI): from 350 to 380 nm, in particular from 355 to 380 nm, (CCII): from 350 to 370 nm, in particular from 355 to 370 nm, (CCIII): from 350 to 360 nm, in particular from 355 to 360 nm, (CCIV): from 350 to 400 nm, in particular from 355 to 400 nm, (CCV): from 370 to 420 nm, (CCVI): from 350 to 400 nm, in particular from 355 to 400 nm, (CCVII): from 380 to 420 nm, (CCVIII): from 355 to 390 nm, (CCIX): from 355 to 390 nm, (CCX): from 360 to 420 nm, (CCXI): from 360 to 390 nm, (CCXII): from 355 to 390 nm, (CCXIII): from 355 to 390 nm.

Customary UV absorbers as are described, for example, in U.S. Pat. Nos. 5,280,380 and 5,073,012 on the basis of substituted benzophenones or cinnamic esters have absorption maxima in the range from 300 to 350 nm.

Preference is given to yellow dyes of the formulae (CCI) to (CCVIII), where $R^{201}$ and $R^{202}$ represent, independently of one another, methoxy, ethoxy, propoxy or butoxy, $R^{203}$ and $R^{204}$ represent, independently of one another, hydrogen, methyl or ethyl, $R^{205}$ represents methyl, ethyl, propyl, butyl, pentyl, hexyl, octyl, decyl, hydroxyethyl, methoxyethyl, ethoxypropyl, —$CH_2CH_2O$—(CO)—$CH=CH_2$, benzyl, phenylpropyl, methoxy, ethoxy, propoxy, butoxy, pentoxy, hexoxy, octoxy, decoxy, hydroxyethoxy, methoxyethoxy, ethoxypropoxy, —$OCH_2CH_2$—O—(CO)—$CH=CH_2$, benzyloxy or phenylpropoxy, X represents S or N—$R^{206}$, $R^{206}$ and $R^{227}$ represent, independently of one another, methyl, ethyl, propyl, butyl, pentyl, hexyl, heptyl or octyl, $R^{207}$ and $R^{208}$ represent, independently of one another, hydroxyl, methoxy, ethoxy, propoxy, butoxy, benzyloxy or phenoxy, $R^{209}$ and $R^{210}$ represent, independently of one another, methoxy, ethoxy, propoxy, butoxy, hexoxy, methoxyethoxy, methylthio, ethylthio, amino, $NHR^{217}$, phenoxy, cyano, CO—$OR^{217}$, CO—$NR^{217}R^{218}$, $NR^{218}$—CO—$R^{219}$, $NR^{218}$—$SO_2$—$R^{219}$ and $R^{209}$ may also represent hydrogen, methyl, hydroxyethoxy, —$OCH_2CH_2$—O—(CO)—$CH=CH_2$, —O—$(CH_2)_4$—O—(CO)—$C(CH_3)=CH_2$, —NH—(CO)—$C_6H_4$—O—$CH_2CH_2$—O—(CO)—$CH=CH_2$, $R^{211}$ and $R^{212}$ represent, independently of one another, hydrogen, fluorine, chlorine, bromine, methyl, ethyl, methoxy or ethoxy, Het represents benzothiazol-2-yl, benzoxazol-2-yl or 2- or 4-pyridyl, Y represents C—$R^{213}$, $R^{213}$ represents hydrogen, cyano, CO—$R^{219}$, CO—O—$R^{217}$ or CO—$NR^{217}R^{218}$, $R^{214}$ and $R^{215}$ represent, independently of one another, methyl, ethyl, propyl, butyl, hexyl, chloroethyl, methoxyethyl, hydroxyethyl, cyanoethyl, benzyl, phenethyl, phenylpropyl, phenyl; tolyl, methoxyphenyl, chlorophenyl or CO—$R^{219}$ and $R^{214}$ may also represent hydrogen or $CH_2CH_2$—O—(CO)—$C(CH_3)=CH_2$ or $NR^{214}R^{215}$ represents pyrrolidino, piperidino or morpholino, $R^{216}$ represents hydrogen, fluorine, chlorine, bromine, methyl, ethyl, methoxy, ethoxy or NH—CO—$R^{219}$, $R^{217}$ and $R^{218}$ represent, independently of one another, methyl, ethyl, propyl, butyl, hexyl, benzyl, phenethyl, phenylpropyl, phenyl, tolyl, methoxyphenyl or chlorophenyl and $R^{218}$ may also represent hydrogen, $R^{219}$ represents methyl, ethyl, propyl, butyl or phenyl, $R^{220}$ represents methoxy, ethoxy, propoxy or butoxy, $R^{221}$ represents hydrogen or methoxy, $R^{222}$ and $R^{224}$ represent hydrogen, $R^{223}$ represents hydrogen, $R^{225}$ represents hydrogen or chlorine, x represents 4 and $R^{226}$ represents CHO and $R^{227}$ represents butyl, pentyl, hexyl, heptyl or octyl, where the alkyl and alkoxy radicals may be linear or branched, e.g. n-butyl, 2-butyl, tert-butyl.

Particular preference is given to yellow dyes of the formulae (CCI) to (CCVIII), where $R^{201}$ and $R^{202}$ represent methoxy, $R^{203}$ and $R^{204}$ represent methyl, $R^{205}$ represents propyl, butyl, tert-butyl, propoxy or butoxy, X represents N-(2-ethyl-1-hexyl), $R^{207}$ and $R^{208}$ represent hydroxy, $R^{209}$ and $R^{210}$ are identical and represent methoxy, ethoxy, amino, NH-methyl, NH-ethyl, cyano, CO—O-methyl, CO—O-n-butyl, CO—NH-n-butyl, CO—NH-phenyl, NH—CO-n-butyl, NH—CO-tert-butyl or NH—CO-phenyl, $R^{211}$ and $R^{212}$ represent, independently of one another, hydrogen or methyl, Het represents benzothiazol-2-yl or 4-pyridyl, Y represents C—$R^{213}$, $R^{213}$ represents hydrogen, cyano, CO—$NH_2$, acetyl or CO—O-methyl, $R^{214}$ and $R^{215}$ represent, independently of one another, methyl, ethyl, butyl, cyanoethyl, benzyl, phenyl or acetyl, $R^{216}$ represents hydrogen, methyl or methoxy, $R^{220}$ and $R^{221}$ represent, independently of one another, hydrogen, methyl, ethyl, propyl, butyl, methoxy, ethoxy, propoxy or butoxy, $R^{222}$ and $R^{224}$ represent hydrogen, $R^{223}$ represents hydrogen or hydroxy, $R^{225}$ represents hydrogen or halogen, x represents 4 and $R^{226}$ represents CHO or CN.

Very particular preference is given to yellow dyes of the formulae (CCI), (CCV), (CCVI) and (CCVIII).

Preference is likewise given to fluorescent dyes of the formulae (CCIX) to (CCXIII), where $R^{228}$ to $R^{231}$ represent, independently of one another, chlorine or cyano, where two of these radicals may also represent hydrogen, y represents 1, $R^{232}$ represents $C_6$–$C_{10}$-aryl, pyrazol-1-yl, 4-chloropyrazol-2-yl or 1,2,4-triazol-1- or -4-yl, $R^{233}$ represents hydrogen, methoxy, ethoxy, 4-phenyl-5-methyl-1,2,3-triazol-2-yl, 4-ethyl-5-methyl-1,2,3-triazol-2-yl, dimethylamino or diethylamino, $R^{234}$ and $R^{235}$ represent hydrogen or together represent a —CH=CH—CH=CH— bridge, $R^{237}$ and $R^{243}$ represent hydrogen, $R^{238}$ and $R^{239}$ represent, independently of one another, chlorine, acetyl, propionyl or methylsulphonyl, $R^{240}$ and $R^{241}$ represent, independently of one another, hydrogen, methyl, ethyl, propyl or butyl, Z represents O or N—$R^{244}$, D represents —CH=CH—, 1,4-phenylene, thiophene-2,5-diyl or furan-2,5-diyl, $R^{242}$ represents hydrogen, cyano or CO—O-methyl, -ethyl, -propyl or -butyl, z represents 0 or 1 and $R^{244}$ represents methyl, ethyl, propyl or butyl, where the alkyl and alkoxy radicals may be linear or branched, e.g. n-butyl, 2-butyl, tert-butyl.

Particular preference is given to fluorescent dyes of the formulae (CCIX) to (CCXIII),
where $R^{230}$ and $R^{231}$ represent cyano, y represents 1, $R^{232}$ represents phenyl or 4-chloro-pyrazol-1-yl, $R^{233}$ represents methoxy, 4-phenyl-5-methyl-1,2,3-triazol-2-yl, 4-ethyl-5-methyl-1,2,3-triazol-2-yl, dimethylamino or diethylamino, $R^{234}$ and $R^{235}$ represent hydrogen, $R^{228}$, $R^{229}$, $R^{237}$ and $R^{243}$ represent hydrogen, $R^{238}$ and $R^{239}$ represent chlorine, $R^{240}$ and $R^{241}$ are identical and represent hydrogen, methyl or tert-butyl, Z represents O, D represents —CH=CH— or thiophene-2,5-diyl, $R^{242}$ represents CO—O-methyl and z represents 0.

Very particular preference is given to the fluorescent dyes of the formulae (CCIX), (CCX) and (CCXII).

The stability of these organic yellow filters to exposure to daylight can be increased by combining them with UV absorbers which absorb radiation below 350 nm.

In particular, inorganic nanosize particles are suitable for this task.

Nanosize particles are likewise, in particular, suitable as yellow filter.

Suitable nanosize particles are those based on SiC, AlSi, $Fe_2O_3$, $TiO_2$, ZnO, GaP, $CeO_2$, ZnS, $SnO_2$, $Si_yGe_{1-y}$, $W_xMo_{1-x}O_3$, NiO, $Bi_2O_3$, $In_2O_3$, $HfO_2$, $BaTiO_3$, $CaTiO_3$, Ge, AlP, GaN, where $0.7 \leq y<1$ and $0 \leq x<1$.

Nanosize particles which are particularly suitable for the purposes of the invention are the materials based on $TiO_2$, ZnO, $CeO_2$, AlSi, $Fe_2O_3$, $Fe_3O_4$, $W_xMo_{1-x}O_3$, $BaTiO_3$, $CaTiO_3$ or mixtures thereof which are known from the above-cited literature and patent applications.

Particular preference is given to nanosize particles having a mean diameter of less than 500 nm, preferably less than 100 nm, particularly preferably less than 50 nm, very particularly preferably less than 20 nm.

Preference is given to nanosize particles of all previously described materials which have a spherical or almost spherical shape. For the purposes of the present invention, almost spherical refers, for example, to ellipsoids having an axis ratio of up to 1:4, preferably up to 1:2.

Likewise preferred are nanosize particles of all previously described materials which have a core-shell structure. The shell may be organically modified.

The shell comprises, for example, an oxide of the material of the nanosize particle. However, it can also comprise a different material which is transparent in the visible region and whose index of refraction is similar to that of the nanosize particle. The thickness of an oxide layer can be, for example, from 1 to 300 nm.

In a preferred embodiment of the invention, the solid compounds in which silicon is present in a stoichiometric excess have a core-shell structure. Here, it is preferred that this consists of a core of titanium nitride and a shell of silicon, where the proportion by volume of silicon is at least 30% per particle.

The absorption edges of nanosize particles are, for example, in the following range:

$CeO_2$: 380 nm

Si: 380 nm

SiC: 415 nm.

Mixtures of the compounds of the formulae (CCI) to (CCXIII) with nanosize particles are likewise suitable as yellow filters.

To compensate for any yellow cast in the electrochromic device caused by the yellow filter, the light-stabilized electrochromic device of the invention may additionally contain violet to blue components. These can be present in the electrochromic system and/or in one of the plates or films and/or on one of the plates or films. These components can be, for example, soluble, violet or blue dyes.

The fluorescent dyes of the formulae (CCIX) to (CCXIII) used according to the invention can on their part reduce the yellow cast of the electrochromic device.

In a preferred embodiment, the yellow filter used according to the invention, in particular the nanosize particles, additionally contains particles, for example of oxides or nitrides of metals, which absorb more strongly in the red spectral region of 600 nm<$\lambda$<700 nm than in the blue-green spectral region of 400 nm<$\lambda$<550 nm. As such additives, preference is given to particles of titanium nitride having a mean diameter of from 1 nm to 400 nm, preferably from 10 nm to 120 nm, or agglomerates of these titanium nitride primary particles. They can be prepared, for example, as described in U.S. Pat. No. 5,472,477.

In a preferred embodiment, the yellow filter, in particular the nanosize particles, contains silicon particles together with TiN particles having a mean diameter of from 10 to 120 nm. These particles are very effective in the UV-A region and at the same time ensure colour neutrality combined with high transparency. Preference is likewise given to additives in the form of particles of aluminum sodium silicates (ultramarine pigments), for example those obtainable under the name Nubix® pigments (Nubiola S.A.). Furthermore, they can contain iron(III) hexacyanoferrate(II) as additive.

According to the invention, particular preference is given to electrochromic devices in which at least one of the two conductive layers is coated with an electrochromic layer, and also electrochromic devices in which the electrochromic medium is an electrochromic solution or a gel, characterized in that the electrochromic device is protected against light by means of a yellow filter.

Preference is given to light-stabilized electrochromic devices according to the invention in which a) the reducible substance has at least one, preferably at least two, chemically reversible reduction waves in the cyclic voltammogram and the oxidizable substance correspondingly has at least one, preferably at least two, chemically reversible oxidation waves, or b) the reducible substance and the oxidizable substance are covalently bonded to one another via a bridge B or c) the reducible and/or oxidizable substance selected are one in which the reversible transition between the oxidizable form and the reducible form or vice versa is associated with the rupture or formation of a C bond, or d) the reducible substance and/or the oxidizable substance are metal salts or metal complexes of metals which exist in at least two oxidation states, or e) the reducible and/or oxidizable substances are oligomers and polymers which contain at least one of the abovementioned redox systems or pairs of such redox systems as are defined under a) to d), or f) the reducible and/or oxidizable substances used are mixtures of the substances described in a) to e), provided that these mixtures contain at least one reducible and at least one oxidizable redox system.

Selection of the electrochromic compounds $RED_1$ and $OX_2$ and/or mixtures thereof enable any monochromic colours to be obtained. For a polychromic image, two or more such electrochromic devices can be laid flat on top of one another, with each of these devices being able to produce a different colour. Preferably, such a stack is constructed so that the devices which are in contact have a translucent plate in common and this is then conductively coated on both sides and, depending on the design, is divided into segments. For example, a stack then comprises three electrochromic devices made of at least four plates. Switching-on segments on various devices in this stack enables polychromic displays to be obtained. If superposed segments of various such devices are switched on, mixed colours are obtained. Thus, any colours, for example coloured pictures, can be displayed using three basic colours.

$OX_2$ and $RED_1$ which are suitable for the purposes of the invention are substances which, on reduction or oxidation at the cathode or anode in the specified solvent, give products $RED_2$ and $OX_1$ which undergo no subsequent chemical reaction but can, as they are, be reoxidized or rereduced to $OX_2$ and $RED_1$.

The electrochromic compounds $RED_1$ or $OX_2$ in their corresponding switched, coloured state preferably have, apart from the actual strong absorption in the visible region of the light spectrum which is important for the function of the electrochromic device, a further strong absorption in the range from 350 to 450 nm, i.e. in the transition region from ultraviolet light to violet and blue light.

Suitable reducible substances $OX_2$ are, for example

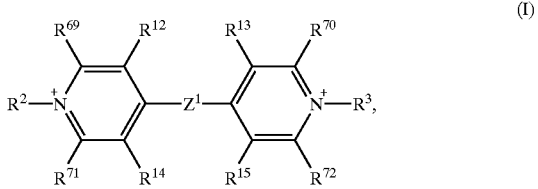
(I)

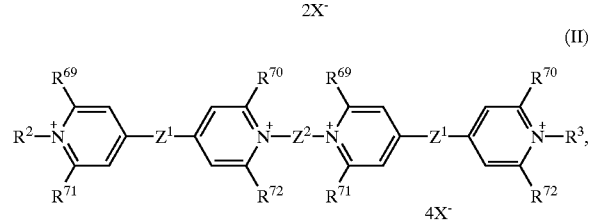
(II)

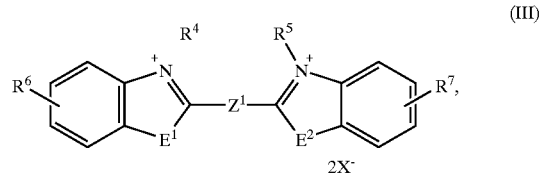
(III)

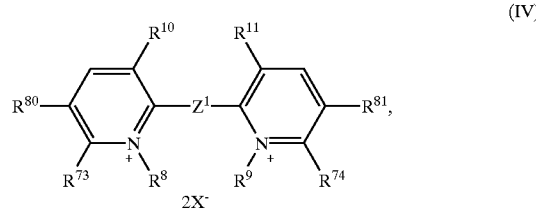
(IV)

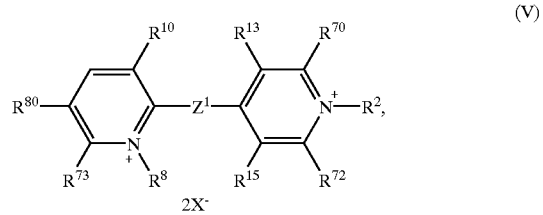
(V)

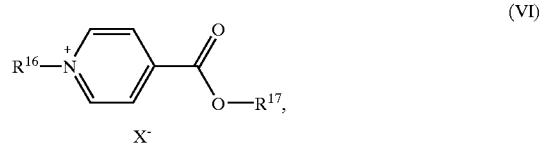
(VI)

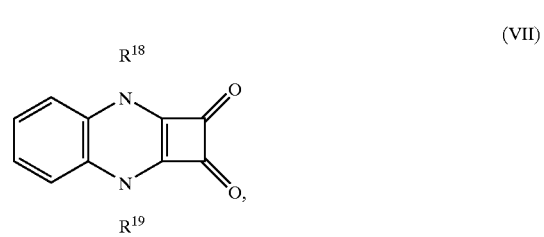
(VII)

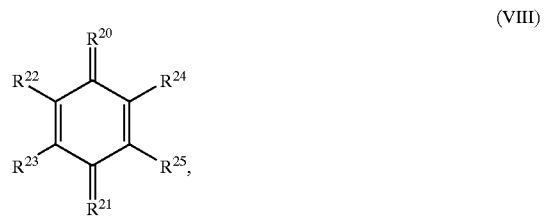
(VIII)

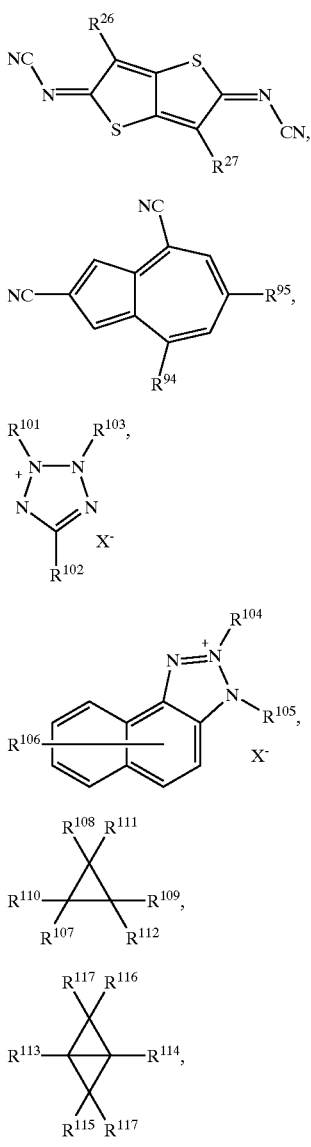
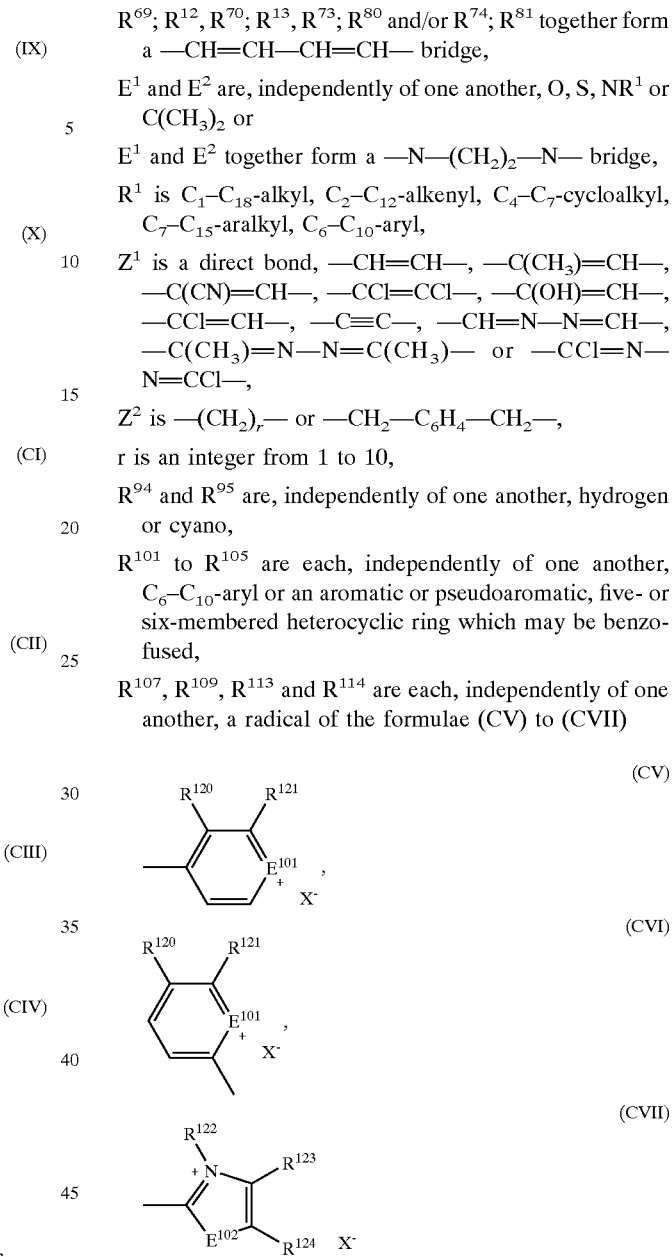

where
- $R^2$ to $R^5$, $R^8$, $R_9$, $R^{16}$ to $R^{19}$ are, independently of one another, $C_1$–$C_{18}$-alkyl, $C_2$–$C_{12}$-alkenyl, $C_4$–$C_7$-cycloalkyl, $C_7$–$C_{15}$-aralkyl or $C_6$–$C_{10}$-aryl or
- $R^4$; $R^5$ or $R^8$; $R^9$ can together form a —$(CH_2)_2$— or —$(CH_2)_3$— bridge,
- $R^6$, $R^7$ and $R^{22}$ to $R^{25}$ are, independently of one another, hydrogen, $C_1$–$C_4$-alkyl, $C_1$–$C_4$-alkoxy, halogen, cyano, nitro or $C_1$–$C_4$-alkoxycarbonyl or
- $R^{22}$; $R^{23}$ and/or $R^{24}$; $R^{25}$ can form a —CH=CH—CH=CH— bridge,
- $R^{10}$; $R^{11}$, $R^{10}$; $R^{13}$, $R^{12}$; $R^{13}$ and $R^{14}$; $R^{15}$ are, independently of one another, hydrogen or, in pairs, a —$(CH_2)_2$—, —$(CH_2)_3$— or —CH=CH— bridge,
- $R^{20}$ and $R^{21}$ are, independently of one another, O, N—CN, $C(CN)_2$ or N—$C_6$–$C_{10}$-aryl,
- $R^{26}$ and $R^{27}$ are hydrogen, $C_1$–$C_4$-alkyl, $C_1$–$C_4$-alkoxy, halogen, cyano, nitro, $C_1$–$C_4$-alkoxycarbonyl or $C_6$–$C_{10}$-aryl,
- $R^{69}$ to $R^{74}$, $R^{80}$ and $R^{81}$ are, independently of one another, hydrogen or $C^1$–$C_6$-alkyl or
- $R^{69}$; $R^{12}$, $R^{70}$; $R^{13}$, $R^{73}$; $R^{80}$ and/or $R^{74}$; $R^{81}$ together form a —CH=CH—CH=CH— bridge,
- $E^1$ and $E^2$ are, independently of one another, O, S, $NR^1$ or $C(CH_3)_2$ or
- $E^1$ and $E^2$ together form a —N—$(CH_2)_2$—N— bridge,
- $R^1$ is $C_1$–$C_{18}$-alkyl, $C_2$–$C_{12}$-alkenyl, $C_4$–$C_7$-cycloalkyl, $C_7$–$C_{15}$-aralkyl, $C_6$–$C_{10}$-aryl,
- $Z^1$ is a direct bond, —CH=CH—, —$C(CH_3)$=CH—, —C(CN)=CH—, —CCl=CCl—, —C(OH)=CH—, —CCl=CH—, —C≡C—, —CH=N—N=CH—, —$C(CH_3)$=N—N=$C(CH_3)$— or —CCl=N—N=CCl—,
- $Z^2$ is —$(CH_2)_r$— or —$CH_2$—$C_6H_4$—$CH_2$—,
- r is an integer from 1 to 10,
- $R^{94}$ and $R^{95}$ are, independently of one another, hydrogen or cyano,
- $R^{101}$ to $R^{105}$ are each, independently of one another, $C_6$–$C_{10}$-aryl or an aromatic or pseudoaromatic, five- or six-membered heterocyclic ring which may be benzofused,
- $R^{107}$, $R^{109}$, $R^{113}$ and $R^{114}$ are each, independently of one another, a radical of the formulae (CV) to (CVII)

- $R^{108}$, $R^{115}$ and $R^{116}$ are each, independently of one another, $C_6$–$C_{10}$-aryl or a radical of the formula (CV),
- $R^{110}$ to $R^{112}$, $R^{117}$ and $R^{118}$ are, independently of one another, $C_1$–$C_4$-alkyl, halogen or cyano,
- $E^{101}$ and $E^{102}$ are, independently of one another, O, S or N—$R^{119}$,
- $R^{119}$ and $R^{122}$ are, independently of one another, $C_1$–$C_{18}$-alkyl, $C_2$–$C_8$-alkenyl, $C_4$–$C_7$-cycloalkyl, $C_7$–$C_{15}$-aralkyl or $C_6$–$C_{10}$-aryl,
- $R^{106}$, $R^{120}$, $R^{121}$, $R^{123}$ and $R^{124}$ are, independently of one another, hydrogen, $C_1$–$C_4$-alkyl, $C_1$–$C_4$-alkoxy, halogen, cyano, nitro or $C_1$–$C_4$-alkoxycarbonyl or
- $R^{120}$, $R^{121}$ or $R^{123}$, $R^{124}$ together form a —CH=CH—CH=CH— bridge and
- $X^-$ is an anion which is redox-inert under the conditions.

Suitable oxidizable substances RED₁ are, for example,

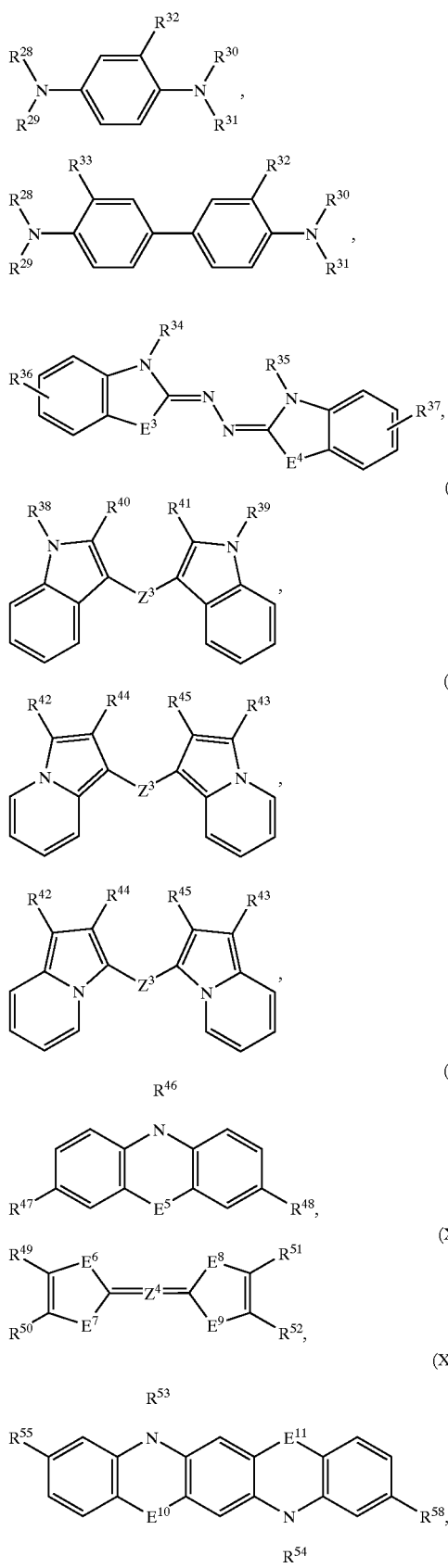

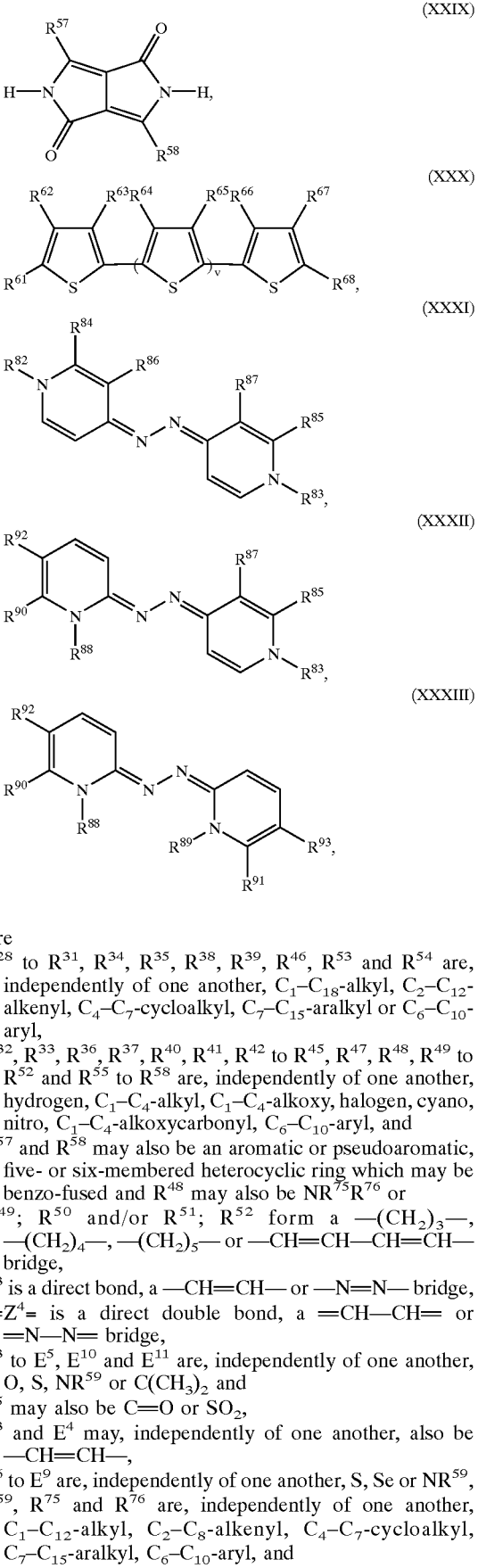

where
R$^{28}$ to R$^{31}$, R$^{34}$, R$^{35}$, R$^{38}$, R$^{39}$, R$^{46}$, R$^{53}$ and R$^{54}$ are, independently of one another, $C_1$–$C_{18}$-alkyl, $C_2$–$C_{12}$-alkenyl, $C_4$–$C_7$-cycloalkyl, $C_7$–$C_{15}$-aralkyl or $C_6$–$C_{10}$-aryl, R$^{32}$, R$^{33}$, R$^{36}$, R$^{37}$, R$^{40}$, R$^{41}$, R$^{42}$ to R$^{45}$, R$^{47}$, R$^{48}$, R$^{49}$ to R$^{52}$ and R$^{55}$ to R$^{58}$ are, independently of one another, hydrogen, $C_1$–$C_4$-alkyl, $C_1$–$C_4$-alkoxy, halogen, cyano, nitro, $C_1$–$C_4$-alkoxycarbonyl, $C_6$–$C_{10}$-aryl, and R$^{57}$ and R$^{58}$ may also be an aromatic or pseudoaromatic, five- or six-membered heterocyclic ring which may be benzo-fused and R$^{48}$ may also be NR$^{75}$R$^{76}$ or R$^{49}$; R$^{50}$ and/or R$^{51}$; R$^{52}$ form a —(CH$_2$)$_3$—, —(CH$_2$)$_4$—, —(CH$_2$)$_5$— or —CH═CH—CH═CH— bridge, Z$^3$ is a direct bond, a —CH═CH— or —N═N— bridge, ═Z$^4$═ is a direct double bond, a ═CH—CH═ or ═N—N═ bridge, E$^3$ to E$^5$, E$^{10}$ and E$^{11}$ are, independently of one another, O, S, NR$^{59}$ or C(CH$_3$)$_2$ and E$^5$ may also be C═O or SO$_2$, E$^3$ and E$^4$ may, independently of one another, also be —CH═CH—, E$^6$ to E$^9$ are, independently of one another, S, Se or NR$^{59}$, R$^{59}$, R$^{75}$ and R$^{76}$ are, independently of one another, $C_1$–$C_{12}$-alkyl, $C_2$–$C_8$-alkenyl, $C_4$–$C_7$-cycloalkyl, $C_7$–$C_{15}$-aralkyl, $C_6$–$C_{10}$-aryl, and $R^{75}$ may also be hydrogen or $R^{75}$ and $R^{76}$ in $NR^{75}R^{76}$ may, together with the N atom to which they are bound, form a five- or six-membered ring which may contain further hetero atoms, $R^{61}$ to $R^{68}$ are, independently of one another, hydrogen, $C_1$–$C_6$-alkyl, $C_1$–$C_4$-alkoxy, cyano, $C_1$–$C_4$-alkoxycarbonyl or $C_6$–$C_{10}$-aryl and $R^{61}$; $R^{62}$ and $R^{67}$; $R^{68}$ may, independently of one another, also form a —(CH$_2$)$_3$—, —(CH$_2$)$_4$— or —CH=CH—CH=CH— bridge or $R^{62}$; $R^{63}$, $R^{64}$; $R^{65}$ and $R^{66}$; $R^{67}$ form a —O—CH$_2$CH$_2$—O— or —O—CH$_2$CH$_2$CH$_2$—O— bridge, v is an integer from 0 to 10,000, $R^{82}$, $R^{83}$, $R^{88}$ and $R^{89}$ are, independently of one another, $C_1$–$C_{18}$-alkyl, $C_2$–$C_{12}$-alkenyl, $C_4$–$C_7$-cycloalkyl, $C_7$–$C_{15}$-aralkyl, $C_6$–$C_{10}$-aryl, $R^{84}$ to $R^{87}$ and $R^{90}$ to $R^{93}$ are, independently of one another, hydrogen or $C_1$–$C_6$-alkyl or $R^{84}$; $R^{86}$, $R^{85}$; $R^{87}$, $R^{90}$; $R^{92}$ and/or $R^{91}$; $R^{93}$ together form a —CH=CH—CH=CH— bridge.

Anions such as $I^-$, $I_3^-$, $Br^-$ and $SCN^-$ are likewise suitable as $RED_1$.

Examples of optionally oligomeric or polymeric redox systems linked via a bridge B are those of the formula

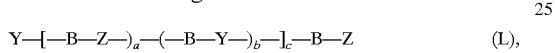

(L), where

Y and Z represent, independently of one another, a radical $OX_2$ or $RED_1$, but at least one Y represents $OX_2$ and at least one Z represents $RED_1$, where $OX_2$ represents the radical of a reversibly electrochemically reducible redox system, and $RED_1$ represents the radical of a reversibly electrochemically oxidizable redox system, B represents a bridge, c represents an integer from 0 to 1000, and a and b represent, independently of one another, an integer from 0 to 100.

Preferably, $(a+b)\cdot c \leq 10,000$.

In the present context, reversibly electrochemically reducible or oxidizable means that electron transfer can occur in the sense of the above definition of $OX_2$ and $RED_1$ according to the invention with or without a change in the σ skeleton.

In particular, the electrochromic compounds of the formula (I) are ones of the formulae

| | |
|---|---|
| OX$_2$-B-RED$_1$ | (La), |
| OX$_2$-B-RED$_1$-B-OX$_2$ | (Lb), |
| RED$_1$-B-OX$_2$-B-RED$_1$ | (Lc), or |
| OX$_2$-(B-RED$_1$-B-OX$_2$)$_d$-B-RED$_1$ | (Ld), | where $OX_2$, $RED_1$ and B are as defined above and d represents an integer from 1 to 5.

$OX_2$ and $RED_1$ in the formulae (L) and (La) to (Ld) are, in particular, radicals of the above-described redox systems of the formulae (I) to (X), (CI) to (CIV) and (XX) to (XXXIII), where bonding to the bridge B is via one of the radicals $R^2$ to $R^{19}$, $R^{22}$ to $R^{27}$, $R^{28}$ to $R^{58}$, $R^{61}$, $R^{62}$, $R^{67}$, $R^{68}$, $R^{83}$, $R^{88}$, $R^{122}$ or, if one of the radicals $E^1$ and $E^2$ represents $NR^1$ or one of the radicals $E^3$ to $E^{11}$ represents $NR^{59}$ or one of the radicals $E^{101}$ to $E^{102}$ represents $NR^{119}$, via $R^1$, $R^{59}$ or $R^{119}$ and the radicals mentioned then represent a direct bond, and B represents a bridge of the formula —(CH$_2$)$_n$— or —[Y$^1_s$(CH$_2$)$_m$—Y$^2$]$_o$—(CH$_2$)$_p$—Y$^3_q$—, which may be substituted by $C_1$–$C_4$-alkyl, $C_1$–$C_4$-alkoxy, halogen or phenyl, Y$^1$ to Y$^3$ represent, independently of one another O, S, NR$^{60}$, COO, CONH, NHCONH, cyclopentanediyl, cyclohexanediyl, phenylene or naphthylene, R$^{60}$ is $C_1$–$C_6$-alkyl, $C_2$–$C_6$-alkenyl, $C_4$–$C_7$-cycloalkyl, $C_7$–$C_{15}$-aralkyl, $C_6$–$C_{10}$-aryl, n is an integer from 1 to 12, m and p are each, independently of one another, an integer from 0 to 8, o is an integer from 0 to 6 and q and s are, independently of one another, 0 or 1.

Very particularly preferably, $OX_2$ and $RED_1$ in the formulae (L) and (La) to (Ld) are radicals of the above-described redox systems of the formulae (I), (V), (XX), (XXII), (XXIII), (XXV), (XXVI) and (XXXIII).

Examples of compounds of the formula (La) are

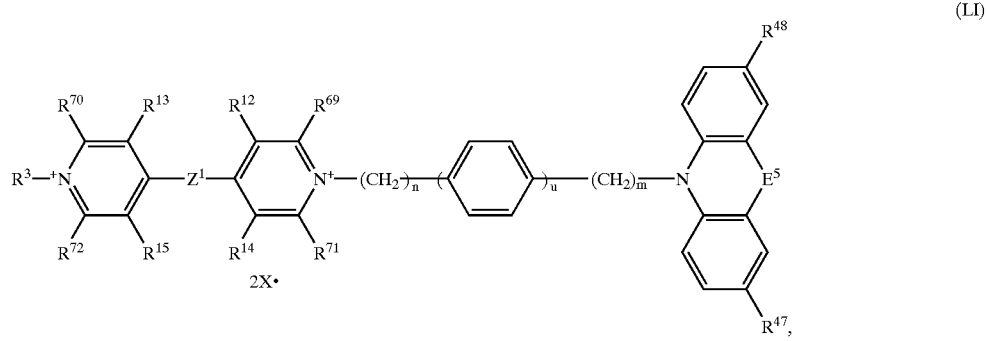

(LI)

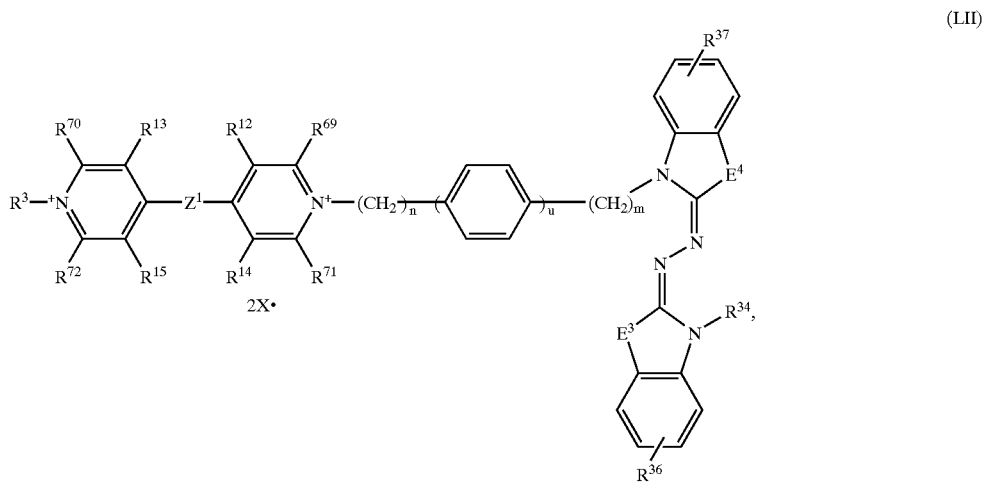
(LII)
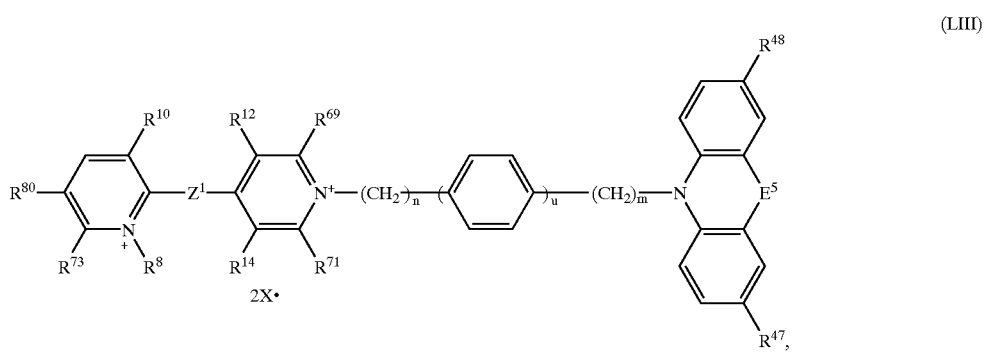
(LIII)
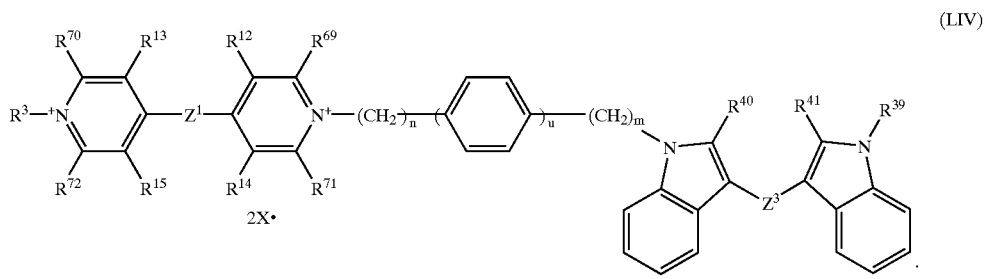
(LIV)
of formula (Lb)

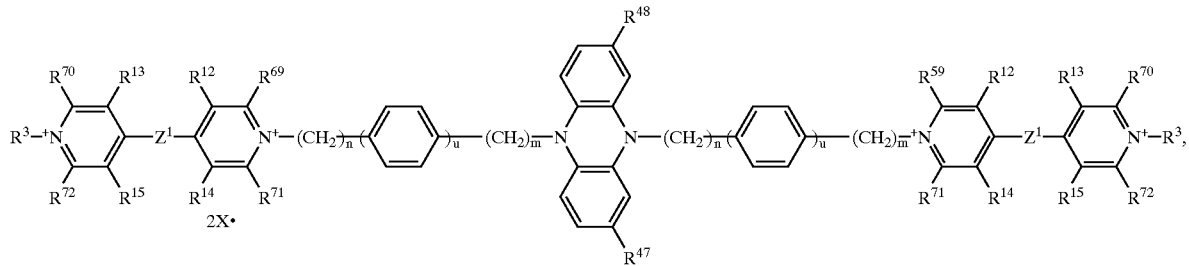
(LV)
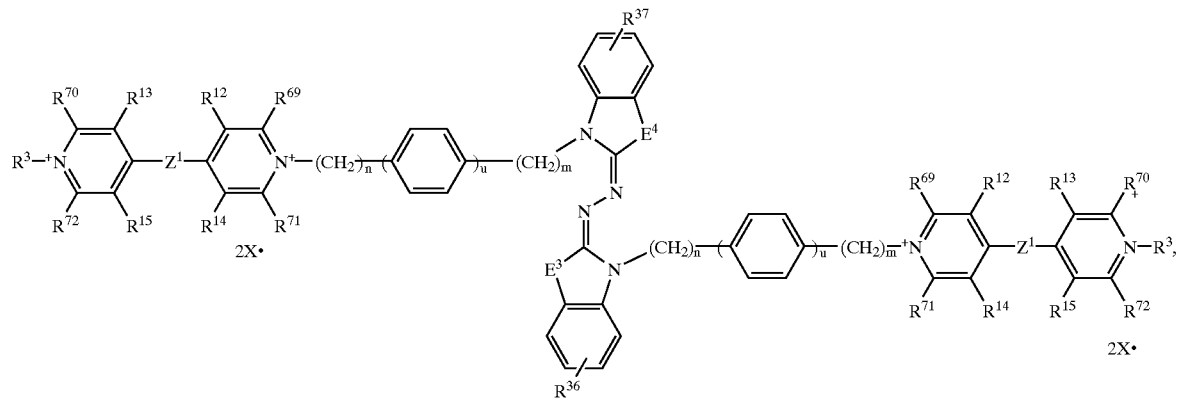
(LVI)
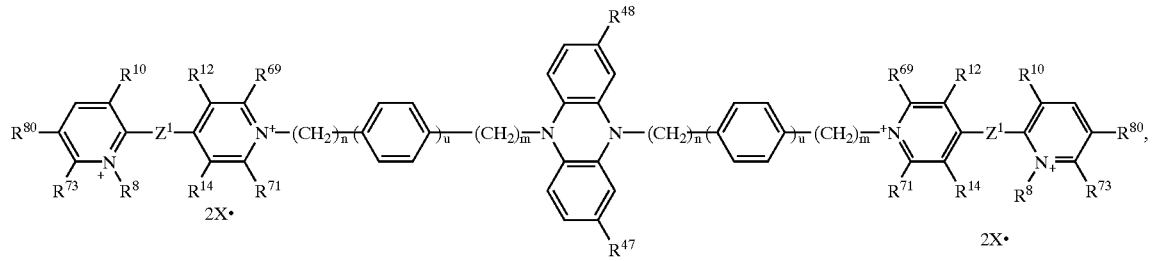
(LVII)
of formula (Lc)

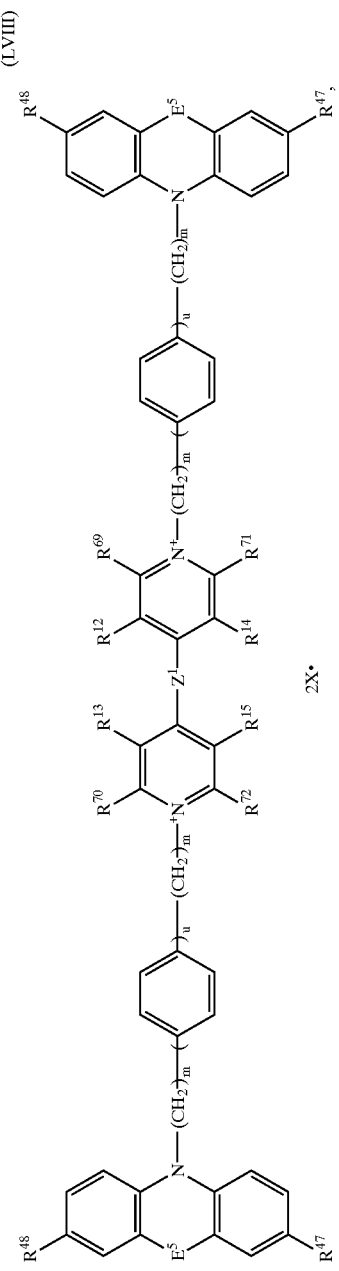
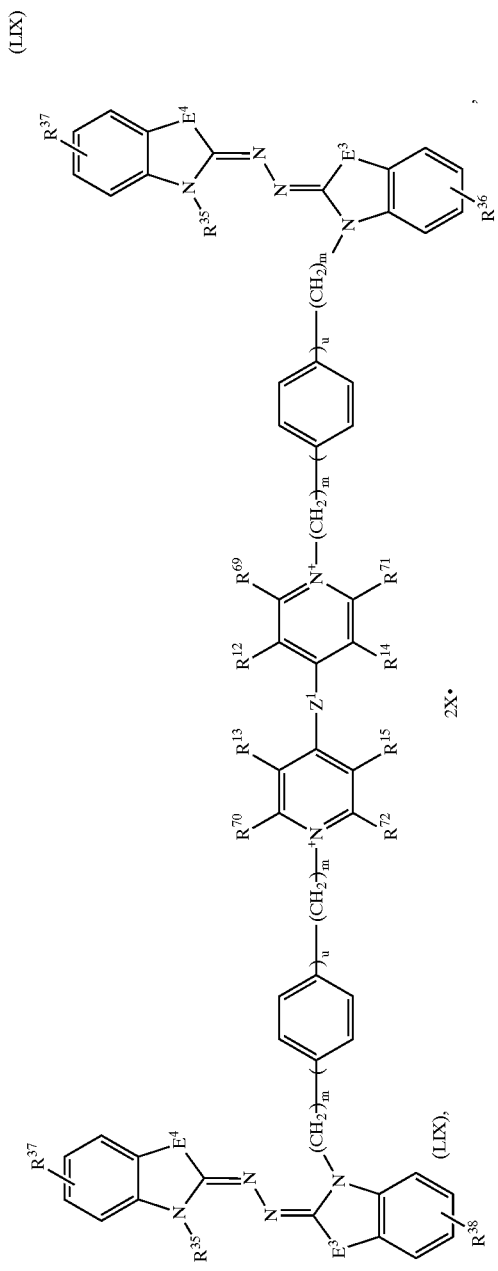

where m represents an integer from 1 to 5, u represents 0 or 1 and the other radicals are as defined above.

In another type of oligomeric or polymeric systems, the groups $OX_2$ and/or $RED_1$ may also be bound, for example as side chains, to a main group, for example a poly(meth) acrylate, silicone, polycarbonate, polyurethane, polyurea, polyester, polyamide, cellulose or other oligomeric or polymeric systems.

Examples of metal salts or metal complexes which can be used as $OX_2$ or $RED_1$ are $Fe^{3+/2+}$, $Ni^{3+/2+}$, $Cu^{2+/+}$, $[Fe(CN)_6]^{3-/4-}$, $Fe_4[Fe(CN)_6]_3^{0/4-}$, $[Co(CN)_6]^{3-/4-}$, $[Fe(cyclopentadienyl)_2]^{0/+}$, $Lu(Pc)^{2+ \ to \ 2-}$ ($PC =$ phthalocyanine), $Fe[Fe(CN)_6]^{0/1-}$.

Suitable counterions for metal ions and cationic complexes are all redox-inert anions $X^-$ as will be described in more detail below, while suitable counterions for the anionic complexes are all redox-inert cations $M^+$, for example alkali metals or quaternary ammonium salts such as $Na^+$, $K^+$, $N(CH_3)_4^+$, $N(C_4H_9)_4^+$, $C_6H_5CH_2N(CH_3)_3^+$ and others.

Preference is likewise given to an electrochromic device which contains mixtures of the electrochromic substances described above in general terms and as preferred. Examples of such mixtures are (I)+(CI)+(XXVI), (I)+(IV)+(XXII), (La)+(I)+(XXVI), (La)+(CI), without this implying any restriction.

The mixing ratios can be varied within wide limits. They allow the optimization of a desired colour or degree of blackness and/or the optimization of the desired dynamics of the device.

In the above definitions of substituents, alkyl radicals, including derivatives such as alkoxy or aralkyl radicals, are preferably ones having from 1 to 12 carbon atoms, in particular from 1 to 8 carbon atoms, unless indicated otherwise. They can be linear or branched and, if desired, bear further substituents such as $C_1$–$C_4$-alkoxy, fluorine, chlorine, hydroxyl, cyano, $C_1$–$C_4$-alkoxycarbonyl or COOH.

Cycloalkyl radicals are preferably ones having from 3 to 7 carbon atoms, in particular 5 or 6 carbon atoms.

Alkenyl radicals are preferably ones having from 2 to 8 carbon atoms, in particular from 2 to 4 carbon atoms.

Aryl radicals, including those in aralkyl radicals, are phenyl or naphthyl, in particular phenyl radicals. They can be substituted by from 1 to 3 of the following radicals: $C_1$–$C_6$-alkyl, $C_1$–$C_6$-alkoxy, fluorine, chlorine, bromine, cyano, hydroxy, $C_1$–$C_6$-alkoxycarbonyl or nitro. Two adjacent radicals can also form a ring.

For the purposes of the present invention, optionally benzo-fused aromatic or pseudoaromatic, five- or six-membered heterocyclic rings are, in particular, imidazole, benzimidazole, oxazole, benzoxazole, thiazole, benzothiazole, indole, pyrazole, triazole, thiophene, isothiazole, benzoisothiazole, 1,3,4- or 1,2,4-thiadiazole, pyridine, quinoline, pyrimidine and pyrazine. They may be substituted by from 1 to 3 of the following radicals: $C_1$–$C_6$-alkyl, $C_1$–$C_6$-alkoxy, fluorine, chlorine, bromine, cyano, nitro, hydroxy, mono- or di-$C_1$–$C_6$-alkylamino, $C_1$–$C_6$-alkoxycarbonyl, $C_1$–$C_6$-alkylsulphonyl, $C_1$–$C_6$-alkanoylamino, phenyl or naphthyl. Two adjacent radicals can also form a ring.

The electrochromic substances are either known (Topics in Current Chemistry, Vol. 92, p. 1–44, (1980), Angew. Chem. 90, 927 (1978), Adv. Mater. 3, 225, (1991), DE-OS 3,917,323, J. Am. Chem. Soc. 117, 8528 (1995), J. C. S. Perkin II 1990, 1777, DE-OS 4,435,211, EP-A 476,456, EP-A 476,457, DE-OS 4,007,058, J. Org. Chem. 57, 1849 (1992) and J. Am. Chem. Soc. 99, 6120, 6122 (1977)) or can be prepared by analogous methods. The compounds of the formula (L) are likewise known (WO 97/30134) or can be synthesized from building blocks known per se, for example according to the following scheme:

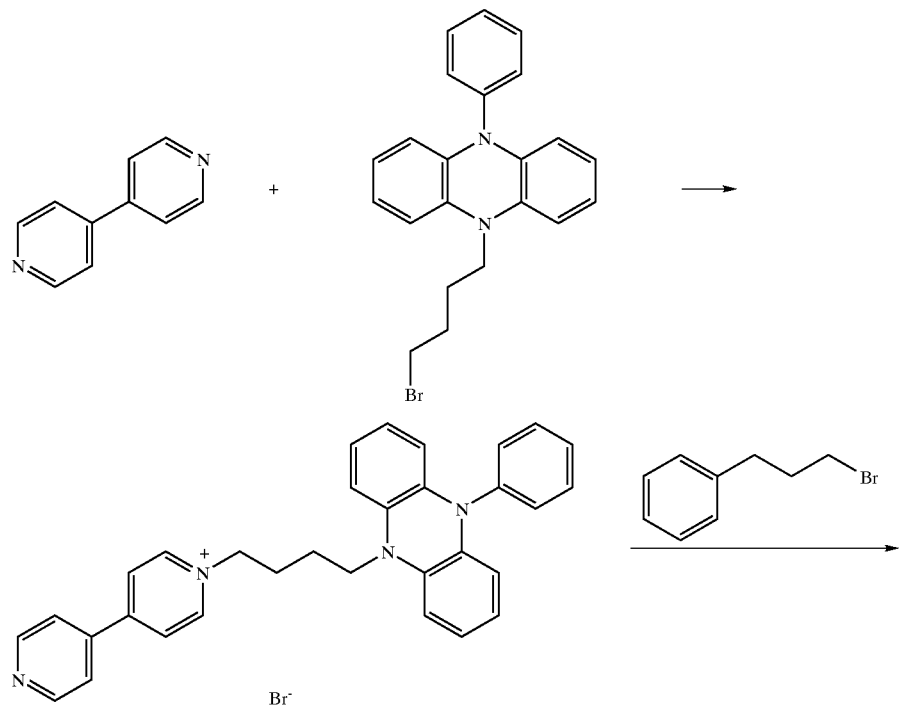

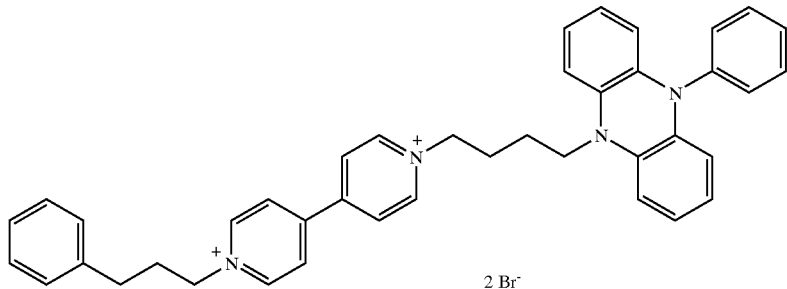

2 Br⁻

Ions such as bromide resulting from the synthesis are subsequently replaced by redox-inert ions.

Particular preference is given to the electrochromic compounds of the formulae (I), (II), (III), (IV), (V), (XXII), (XXIII), (XXVI), (XXVII), (XXXI), (XXXII), (XXXIII), and also the bridge compounds of the formula (L) containing at least one of the formulae as $OX_2$ or $RED_1$.

When making this selection and likewise when making the subsequent particular and very particular selections of electrochromic compounds, it always has to be ensured that the electrochromic medium contains at least one $OX_2$ and at least one $RED_1$. If, for example, $OX_2$=formula (I), then the electrochromic medium must also contain an $RED_1$, preferably selected from among the preferred $RED_1$ of the formulae (XXII), (XXIII), (XXVI), (XXVII), (XXXI), (XXXII), and (XXXIII), or else selected from among the abovementioned general range of $RED_1$ of the formulae (XX) to (XXXIII) or the abovementioned metal salts, complexes or anions X⁻ which are suitable as $RED_1$. This applies analogously to the preferred and particularly preferred $RED_1$.

Very particular preference is given to the electrochromic compounds of the formulae (I), (IV), (V), (XXII), (XXIII), (XXVII), (XXIII),
where
$R^2$, $R^3$, $R^8$ and $R^9$ are, independently of one another, methyl, ethyl, propyl, butyl, pentyl, hexyl, heptyl, benzyl, phenethyl, phenylpropyl, phenyl, 2-methylphenyl or 2,6-dimethylphenyl or
$R^8$ and $R^9$ together form a —(CH$_2$)$_2$— or —(CH$_2$)$_3$— bridge,
$R^{10}$ to $R^{15}$ are hydrogen,
$R^{69}$ to $R^{73}$, $R^{80}$ and $R^{81}$ are, independently of one another, hydrogen or methyl or
$R^{12}$; $R^{69}$, $R^{13}$; $R^{70}$, $R^{73}$; $R^{80}$ and/or $R^{74}$; $R^{81}$ form a —CH=CH—CH=CH— bridge,
$Z^1$ is a direct bond or —CH=CH—
$X^1$ is an anion which is redox-inert under the conditions,
$R^{34}$, $R^{35}$, $R^{38}$, $R^{39}$, $R^{88}$ and $R^{89}$ are, independently of one another, methyl, ethyl, propyl, butyl, benzyl, phenethyl, phenylpropyl or phenyl,
$R^{36}$ and $R^{37}$ are hydrogen,
$Z^3$ is a direct bond or a —CH=CH— bridge,
$Z^4$ is a direct double bond,
$R^{40}$ and $R^{41}$ are identical and are hydrogen or methyl,
$E^3$ and $E^4$ are identical and are S, N—$R^{59}$ or C(CH$_3$)$_2$
$E^6$ to $E^9$ are identical and are S
$R^{49}$ to $R^{52}$ are, independently of one another, hydrogen, methyl, cyano or methoxycarbonyl $R^{49}$; $R^{50}$ and/or $R^{51}$; $R^{52}$ form a —(CH$_2$)$_3$— or —CH=CH—CH=CH— bridge,
$R^{90}$ to $R^{93}$ are hydrogen or
$R^{90}$, $R^{92}$ and/or $R^{91}$; $R^{93}$ form a —CH=CH—CH=CH— bridge and
$R^{59}$ is methyl, ethyl propyl or butyl,
and also the bridged compounds of the formula (L), in particular the formula (La), containing one of the above formulae as $OX_2$ or $RED_1$, where
B is —(CH$_2$)$_n$— and
n is an integer from 3 to 6.

Electrochromic compounds which are very especially suitable for the purposes of the invention are those of the formula (I),
where
$R^2$ and $R^3$ are identical and are methyl, ethyl, butyl, heptyl or phenylpropyl,
$R^{12}$ to $R^{15}$ and $R^{69}$ to $R^{72}$ are hydrogen,
$Z^1$ is a direct bond and
X⁻ is a redox-inert anion or I⁻.

Likewise very especially suitable for the purposes of the invention are the electrochromic compounds of the formula (La),
where
$OX_2$ represents a radical of the formula (I),
$RED_1$ represents a radical of the formula (XXVI) and
B represents —(CH$_2$)$_n$—,
where
n is an integer from 3 to 6,
$R^2$ and $R^{46}$ are direct bonds to B,
$R^3$, $R^{12}$ to $R^{15}$, $R^{69}$ to $R^{72}$, $Z^1$ and X⁻ have the above especially suitable meanings,
$R^{47}$ and $R^{48}$ are hydrogen,
$E^5$ is NR$^{59}$ and
$R^{59}$ is methyl, ethyl, butyl, heptyl, phenylpropyl or phenyl.

The light-stabilized electrochromic device of the invention preferably contains, in its electrochromic medium, at least one solvent in which the electrochromic substances, if desired an electrolyte salt and, if desired, further additives are dissolved. The solvent may also be thickened to form a gel, for example by means of polyelectrolytes, porous solids or nanosize particles having a large active surface area.

Suitable solvents are all solvents which are redox-inert at the voltages selected, which cannot release any electrophiles or nucleophiles or themselves react as sufficiently strong electrophiles or nucleophiles and could thus react with the coloured radical ions. Examples are propylene carbonate, γ-butyrolactone, acetonitrile, propionitrile, benzonitrile, glutaronitrile, methylglutaronitrile, 3,3'-oxydipropionitrile, hydroxypropionitrile, dimethylformamide, N-methylpyrrolidone, sulpholane, 3-methylsulpholane and mixtures thereof. Preference is given to propylene carbonate, benzonitrile and mixtures of these with one another or with glutaronitrile or 3-methylsulpholane. Particular preference is given to propylene carbonate. Benzonitrile is likewise particularly preferred.

The electrochromic solution may contain at least one inert electrolyte salt. Particularly when at least one of the substances of the redox pair $RED_1/OX_2$ is ionic in nature, the addition of an electrolyte salt can be omitted.

Suitable inert electrolyte salts are lithium, sodium and tetraalkylammonium salts, in particular the latter. The alkyl groups can have from 1 to 18 carbon atoms and be identical or different. Preference is given to tetrabutylammonium. Suitable anions for these salts, and also as anions $X^-$ in the formulae (I) to (VI), (CI), (CII) and (CV) to (CVII) and in the metal salts, are all redox-inert, colourless anions.

Examples are tetrafluoroborate, tetraphenylborate, cyanotriphenylborate, tetramethoxyborate, tetrapropoxyborate, tetraphenoxyborate, perchlorate, chloride, nitrate, sulphate, phosphate, methanesulphonate, ethanesulphonate, tetradecanesulphonate, pentadecanesulphonate, trifluoromethanesulphonate, perfluorobutanesulphonate, perfluorooctanesulphonate, benzenesulphonate, chlorobenzenesulphonate, toluenesulphonate, butylbenzenesulphonate, tert-butylbenzenesulphonate, dodecylbenzenesulphonate, trifluoromethylbenzenesulphonate, hexafluorophosphate, hexafluoroarsenate, hexafluorosilicate, 7,8- or 7,9-dicarbanido-1- or -2-undecaborate, which may be substituted on the B and/or C atoms by one or two methyl, ethyl, butyl or phenyl groups, dodecahydro-dicarba-2-dodecaborate or B-methyl-C-phenyl-dodecahydro-dicarba-1-dodecaborate.

Likewise suitable, also as anions $X^-$ in the formulae (I) to (VI), (CI), (CII) and (CV) to (CVII) and in the metal salts, are the abovementioned anions which can also assume the role of a $RED_1$, for example $I^-$, $I_3^-$.

The electrolyte salts are preferably used in a concentration of from 0 to 1 mol/l.

As further additives, it is possible to use thickeners to control the viscosity of the electroactive solution. This can be of importance for avoiding segregation, i.e. the formation of streaky or spotty colour on prolonged operation of the electrochromic device in the switched-on state, and for controlling the bleaching rate after switching off the power.

Suitable thickeners are all compounds which are customary for this purpose, for example polyacrylate, polymethacrylate (Luctite L®), polycarbonate or polyurethane.

Further possible additives for the electrochromic solution are UV absorbers to provide the sometimes-desired protection against UV light (<350 nm). Examples are UVINUL® 3000 (2,4-dihydroxybenzophenone, BASF), SANDUVOR® 3035 (2-hydroxy-4-n-octyloxybenzophenone, Clariant), Tinuvin® 571 (2-(2H-benzotriazol-2-yl)-6-dodecyl-4-methylphenol, Ciba), Cyasorb 24™ (2,2'-dihydroxy-4-methoxybenzophenone, American Cyanamid Company), UVINUL® 3035 (ethyl 2-cyano-3,3-diphenylacrylate, BASF), UVINUL® 3039 (2-ethylhexyl 2-cyano-3,3-diphenylacrylate, BASF), UVINUL® 3088 (2-ethylhexyl p-methoxycinnamate, BASF), CHIMASSORB® 90 (2-hydroxy-4-methoxybenzophenone. Ciba).

Preference is given to the last four mentioned. Likewise preferred are mixtures of UV absorbers, for example of the last four mentioned. Particular preference is given to a mixture of UVINUL® 3039 and CHIMASSORB® 90.

The UV absorbers are used in concentrations of from 0.01 to 2 mol/l, preferably from 0.04 to 1 mol/l.

The electrochromic solution contains the electrochromic substances $OX_2$ and $RED_1$, in particular those of the formulae (I) to (X), (XX) to (XXXIIII), (CI) to (CIV) and (L), in a concentration in each case of at least $10^{-4}$ mol/l, preferably from 0.001 to 0.5 mol/l. The total concentration of all electrochromic substances present is preferably less than 1 mol/l.

The yellow filters used according to the invention, in particular the yellow dyes of the formulae (CCI) to (CCVIII), can likewise be dissolved in the electrochromic medium. They are used in a concentration of from 0.01 to 2 mol/l, preferably from 0.04 to 1 mol/l.

However, they can also be dissolved or finely dispersed in the plates or films if the plates or films are made of plastic. Suitable materials are polycarbonate, polymethyl methacrylate, polyester, polyolefin, polyacetate or cellulose derivatives. The yellow dyes of the formulae (CCI) to (CCVIII) and the fluorescent dyes of the formulae (CCIX) to (CCXIII) are used in a concentration of from 0.01% by weight to 30% by weight, preferably from 0.1 to 20% by weight.

However, they can also be dissolved or finely dispersed in a coating on these plates or films. This mode of use is particularly preferred. The coatings are generally applied to the outer side of the electrochromic device, i.e. on the side of the plates or films which is not conductively coated. Suitable coating materials are all transparent materials which adhere well to the plates or films, for example plastics or surface coating compositions, e.g. polyurethanes, polyvinyl alcohol, polyvinyl acetate, polyacrylates, polymethacrylates, polyesters, polyamide, polyacrylonitrile or corresponding mixed polymers or copolymers, etc. However, these coating materials can also be films which are applied to the plates or films by means of adhesives. The coating materials have a thickness of from 0.1 to 500 μm. The yellow dyes of the formulae (CCI) to (CCXIII) are used in concentrations of from 0.01% by weight to 30% by weight in the coating materials.

The yellow dyes and/or fluorescent dyes can be used in the electrochromic solution and/or in the plates or films and/or in the coating materials. They can also be mixed with one another or various yellow dyes and/or fluorescent dyes can be employed in the various modes of use.

The nanosize particles are preferably used in the form of a dispersion in the plates or films and/or in the coating materials. However, they can also be dispersed in the electrochromic system.

When the nanosize particles are employed in the plates or films, the latter should be made of plastic. Suitable materials are described above. The nanosize particles are used in a concentration of from 0.001 to 30 atom %, preferably from 0.01 to 10 atom %.

When they are employed in coating materials, which is particularly preferred, use is made of materials which have already been mentioned above. The nanosize particles are used in concentrations of from 0.001 to 30 atom %, preferably from 0.01 to 10 atom %.

The nanosize particles can be incorporated into such materials by well-known methods, for example as described in WO-A 95/09 895, WO-A 92/21 315, EP-A 0 628 303.

In addition, UV absorbers as have been described above may also be present in the plates or films and/or coating materials. They serve to protect the materials of the plates, films or coatings against light and also to protect the yellow dyes used according to the invention against UV radiation.

However, it is also possible to use, possibly in addition, other light stabilizer materials such as quenchers or free radical scavengers as are customary in the polymer field, for example UVINUL® 4049H (BASF), UVINUL® 4050H (BASF).

The electrochromic device of the invention is operated using a constant, pulsed or variable-amplitude, for example sinusoidal, direct current. The voltage depends on the desired depth of colour, but particularly on the reduction or oxidation potentials of the $OX_2$ and RED, used. Such potentials can be taken, for example, from Topics in Current Chemistry, Volume 92, pp. 1–44 (1980) or Angew. Chem. 90, 927 (1978) or the literature cited therein. The difference in their potentials is a guide to the voltage required, but the electrochromic device can be operated at a lower or higher voltage. In many cases, e.g. when using $OX_2$=formula (I) or (V) and $RED_1$=formula (XX), (XXII), (XXVI) or (XXVII) or their linkage via a bridge as in formula (L), in particular formulae (La) to (Ld), this potential difference required for operation is $\leq 1$ V. Such electrochromic devices can therefore be supplied in a simple way with power from photovoltaic silicon cells.

When the voltage is switched off, the electrochromic device of the invention returns to its original state. This extinguishing can be considerably accelerated by short-circuiting the segments or plates to which power has been supplied. The display can also be extinguished very quickly by repeatedly reversing the polarity of the voltage, if desired with simultaneous lowering of the voltage.

Varying the layer thickness of the electrochromic device, the viscosity of the electrochromic solution and/or the diffusion or drift performance of the electrochromic substances enables the switching-on and switching-off times of the display device to be influenced within wide limits. Thus, for example, thin layers have shorter switching times than thick layers. This makes it possible to construct devices which switch quickly or slowly and thus to match them optimally to the respective application.

In the case of slow devices, in particular display devices, a power-saving or refresh mode can be used for maintaining the displayed information in the switched-on state. After the information to be displayed has been generated, for example by means of a constant DC voltage or a DC voltage which is modulated or pulsed at high frequency, the device is switched over to a pulsed or changing DC voltage of low frequency; during the phases in which the voltage is zero, the contacts of the segments are not short-circuited. This low frequency can be, for example, in the region of 1 Hz or less and the duration of the switching-on and switching-off phases does not have to be the same, e.g. the switching-off phases can be significantly longer. Since the depth of colour of the displayed information decreases only slowly during the power pauses in the non-short-circuited state, relatively short power impulses are sufficient to make up these losses again in the subsequent refresh phase. In this way, one obtains a flicker-free image with a virtually constant depth of colour which can be maintained using only a fraction of the power which would be consumed if current were to flow continuously.

Examples of specific embodiments of the abovementioned types 1 and 2 are the following, which are likewise subject matter of the invention if they are light-stabilized by means of a yellow filter.

Type 1: (Unmirrored)

From the field of light protection/light filters: windows for buildings, road vehicles, aircraft, railway vehicles, ships, skylights, automobile sunroofs, glazing of greenhouses and conservatories, light filters of any type;

from the field of safety/security: screens for room partitions, for example in offices, road vehicles, aircraft, railway vehicles, darkenable windows, for example on bank counters, door glazing, visors for motorcycle or pilots' helmets;

from the field of design: glazing of ovens, microwave appliances, other household appliances, furniture;

from the field of displays: analogue voltage displays, as battery testers, fuel gauges, temperature displays, etc.

Type 1: (Mirrored)

Mirrors of any type, for example for road vehicles, railway vehicles, in particular planar, spherical, aspherical mirrors and combinations thereof, for example spherical/aspherical mirror glazing in furniture.

Type 2

Display devices of any type, for example segmented or matrix displays, for example for clocks, computers, electrical appliances, electronic appliances such as radios, amplifiers, TVs, CD players, destination displays in buses and trains, departure boards in railways stations and airports, flat VDUs, all applications mentioned under types 1 and 2 which include at least one switchable, static or variable display device, for example dividing windows with displays such as "Please do not disturb", "Position closed", for example automobile mirrors which display information of any type such as indications of the temperature or faults in the vehicle, for example oil temperature, open doors, time, compass direction.

The invention further provides electrochromic substances of the formula

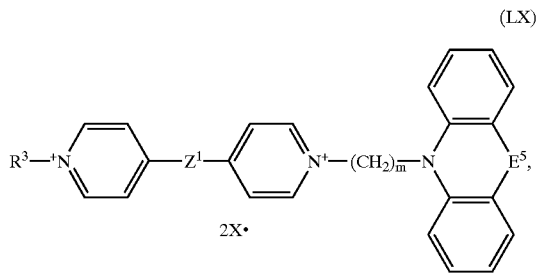

where

R³ is —(CH₂)₃—C₆H₅ or —(CH₂)₄—C₆H₅,
Z¹ is a direct bond,
E⁵ is N—C₆H₅, N—(CH₂)₃—C₆H₅ or N—(CH₂)₄—C₆H₅,
m is an integer from 3 to 5 and
X⁻ is an anion which is redox-inert under the conditions.

Particular preference is given to electrochromic substances of the formula (LX), where R³ is —(CH₂)₃—C₆H₅,
Z¹ is a direct bond,
E⁵ is N—C₆H₅,
m is an integer from 3 to 5 and
X⁻ is an anion which is redox-inert under the conditions.

Very particular preference is given to electrochromic substances of the formula (LX), where R³ is —(CH₂)₃—C₆H₅,
Z¹ is a direct bond,
E⁵ is N—C₆H₅,
m is 4 and
X⁻ is BF₄⁻.

These novel electrochromic substances of the formula (LX) have a higher light stability compared with similar known compounds, e.g. those of the formula (LX) in which R³ is benzyl.

EXAMPLES

Example 1

A cell was constructed as shown in FIG. 1. This was done using two glass plates 1 and 2 which are coated with ITO on one surface.

A mixture of 97% of photocurable epoxy adhesive DELO-Katiobond® 4594 (DELO Industrieklebstoffe, Landsberg) and 3% of glass spheres having a diameter of 200 μm was applied in the form of a peripheral strip 3 to the ITO-coated side of the glass plate 1 so as to leave a 2 mm wide opening 4. The glass plate 2 was then laid onto the bead of adhesive with the ITO layers of the two plates 1 and 2 facing one another so as to give a geometry as shown in FIG. 1. The adhesive was cured by means of illumination with daylight for 10 minutes in the vicinity of a window and subsequently for 20 minutes at 105° C. without illumination.

A dish was filled under a nitrogen atmosphere with a solution which was 0.02 molar in the electrochromic compound of the formula

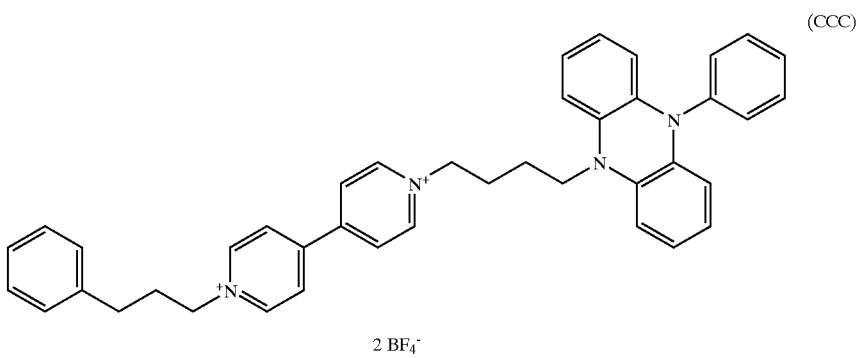

and 0.1 molar in each of the UV absorbers of the formulae

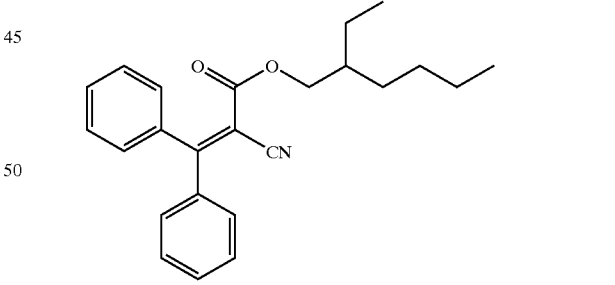

and

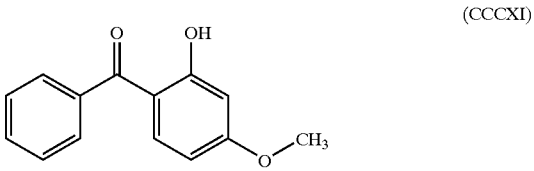

in anhydrous, oxygen-free propylene carbonate and contained 2% by weight of the yellow filter of the formula

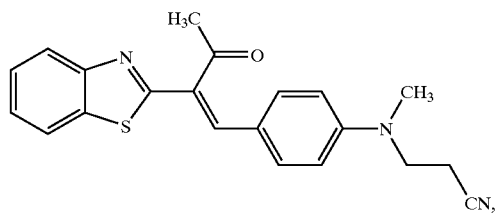

(CCCXX)

having a $\lambda_{max}$ of 383 nm.

The cell was then stood vertically into the dish under a nitrogen atmosphere so that the opening 4 was located below the surface of the liquid. The dish together with the cell was placed in a desiccator. This was evacuated to 0.05 mbar and nitrogen was then carefully admitted. During the admission of nitrogen, the electrochromic solution rose through the opening 4 into the cell and filled the entire volume except for a small bubble. The cell was taken from the solution, cleaned around the opening 4 under nitrogen by wiping it with a paper towel and sealed using the photochemically curable acrylate adhesive DELO-Photobond®4497 (DELO Industrieklebstoffe, Landsberg). The adhesive was subsequently illuminated for 1 minute under a nitrogen atmosphere by means of a DELOLUX®03 lamp (DELO Industrieklebstoffe, Landsberg) which was located at a distance of 8 cm from the opening 4 and curing was completed overnight at room temperature under a nitrogen atmosphere.

On application of a voltage of 0.9 V to two plates 1 and 2, the cell quickly became deep greenish blue. On switching off the voltage and short-circuiting the contacts, the colour quickly disappeared again.

Example 1a (Comparison)

A cell was constructed as described in Example 1, but without the yellow filter of the formula (CCCXX).

Light Stability Test

To test the light stability, cells as described in Example 1 together with reference cells as described in Example 1 a were illuminated at an operating voltage of 0.9 V in a Suntest CPS+ test apparatus from Atlas, Linsengericht-Altenhaßlau, equipped with the filter A and using an irradiation power of 765 W/m².

Before commencement of irradiation, absorption spectra of each cell were recorded in the switched (0.9 V) state and the unswitched state (0 V) using a Cary 4G absorption photometer (Varian, Darmstadt).

Irradiation was carried out for successive intervals which doubled each time (30 minutes, 1 hour, 2 hours, 4 hours, 8 hours, 16 hours), so that each test cell had been irradiated for a total period of 31.5 hours at the end. After each irradiation interval, absorption measurements were again carried out in the switched and unswitched states. These measurement were used to produce difference spectra by plotting the spectra recorded at the particular time minus the starting spectra both in the switched state and the unswitched state.

The damage to the cell was defined by the decrease in the electrochromic swing, i.e. the decrease in the transmission change at a particular wavelength.

The maximum wavelength at 605 nm was evaluated. In evaluating the difference spectra account has to be taken of the fact that changes in the transmission in the unswitched state also appear in the difference spectra of the switched state and have to be subtracted there.

The following table shows the decrease in the electrochromic swing versus the cumulative irradiation time for the cell according to the invention with the yellow filter (as described in Example 1) and, for comparison, that without a yellow filter (as described in Example 1a).

| In % | 0 h | 0.5 h | 1.5 h | 3.5 h | 7.5 h | 15.5 h | 31.5 h |
|---|---|---|---|---|---|---|---|
| Cell with yellow filter | 100 | 100 | 100 | 100 | 100 | 98 | 60 |
| Cell without yellow filter | 100 | 70 | 50 | 43 | 35 | — | — |

If significant damage to the cell is defined as a drop of 20% in the electrochromic swing, the cell without a yellow filter has a stability of 19 minutes. With the yellow filter, this stability increases to 25 hours, corresponding to an improvement by a factor of 80.

In a completely analogous fashion, the compounds Examples 1-1 to 1-15 were used as electrochromic substances and yellow filters:

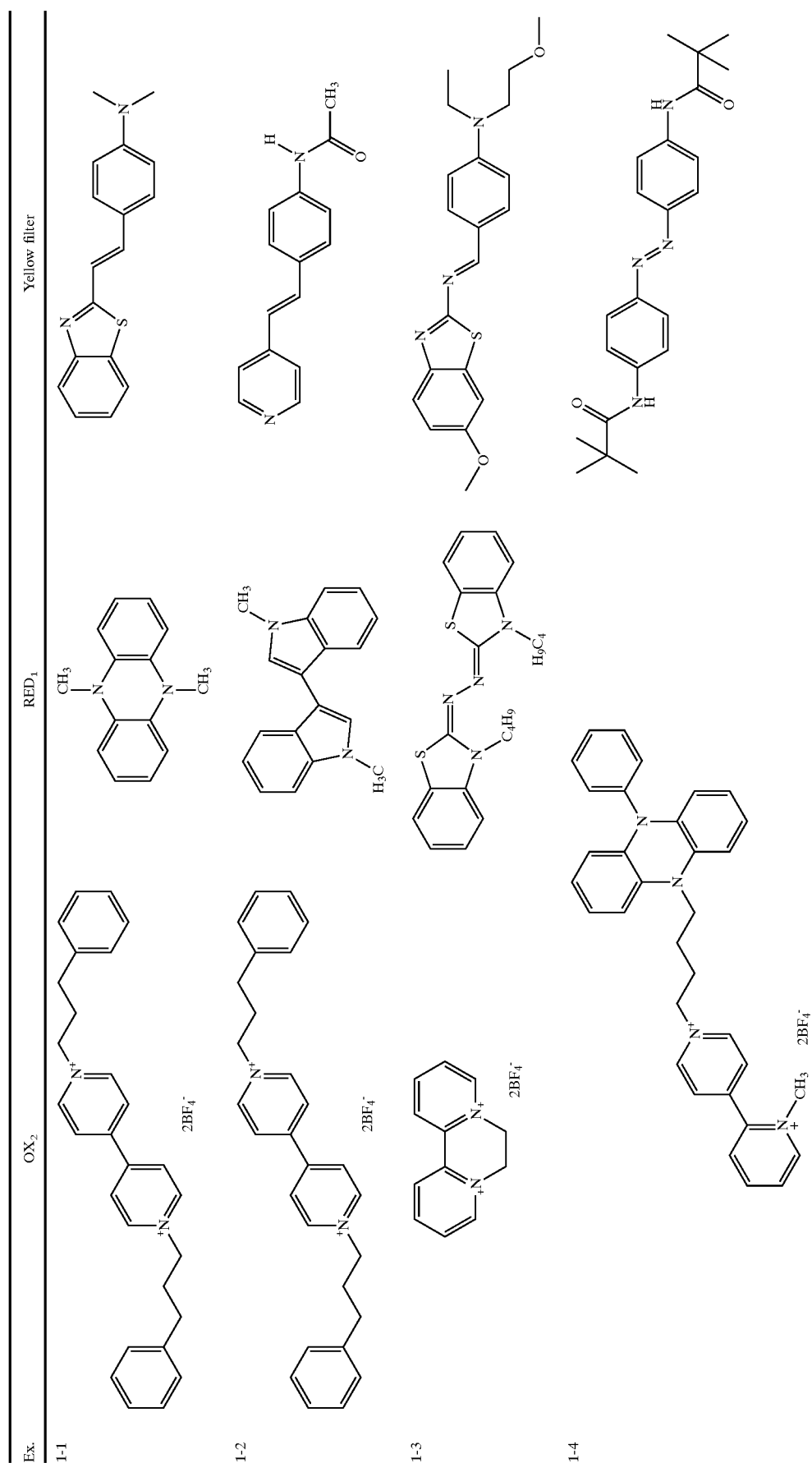

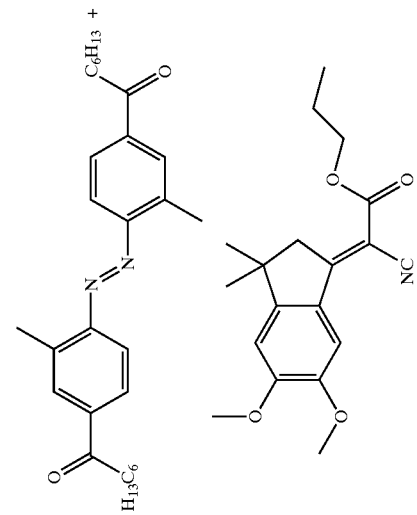

-continued

| Ex. | OX$_2$ | RED$_1$ | Yellow filter |
|---|---|---|---|
| 1-7 | | | |
| 1-8 | | | |
| 1-9 | | | |

| Ex. | OX₂ | RED₁ | Yellow filter |
|---|---|---|---|
| 1-10 | | | |
| 1-11 | | ferrocene | |
| 1-12 | | | |

-continued

| Ex. | OX$_2$ | RED$_1$ | Yellow filter |
|---|---|---|---|
| 1-13 | | | |
| 1-14 | | ferrocene | |
| 1-15 | | | |

Example 2

As in Example 1, use was made of two plates which are coated with ITO on one side. On the other side, a PU coating composition comprising Desmodur and Desmophen (Bayer AG) and containing 0.9 per cent by weight of the yellow filter of the formula

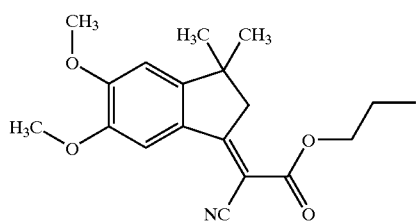

(CCCXXI)

was applied in a wet film thickness of 240 μm by doctor blade coating. The films were dried overnight at 130° C.

A cell was constructed from these plates using a procedure analogous to Example 1.

This cell was filled with a solution which was 0.02 molar in the electrochromic compound of the formula (CCC) (see Example 1) in anhydrous, oxygen-free propylene carbonate. The cell was sealed as described in Example 1.

Example 2a (Comparison)

A cell was constructed as in Example 2, but use was made of glass plates which were coated only with ITO.

Light Stability Test

The light stability of the cells from Examples 2 (according to the invention) and 2a were tested as described above, under the same test conditions. The cell of Example 2 had better light stability than the cell of Example 2a.

In a completely analogous way, the compounds of Examples 2-1 to 2-12 were used as electrochromic substances and yellow filters.

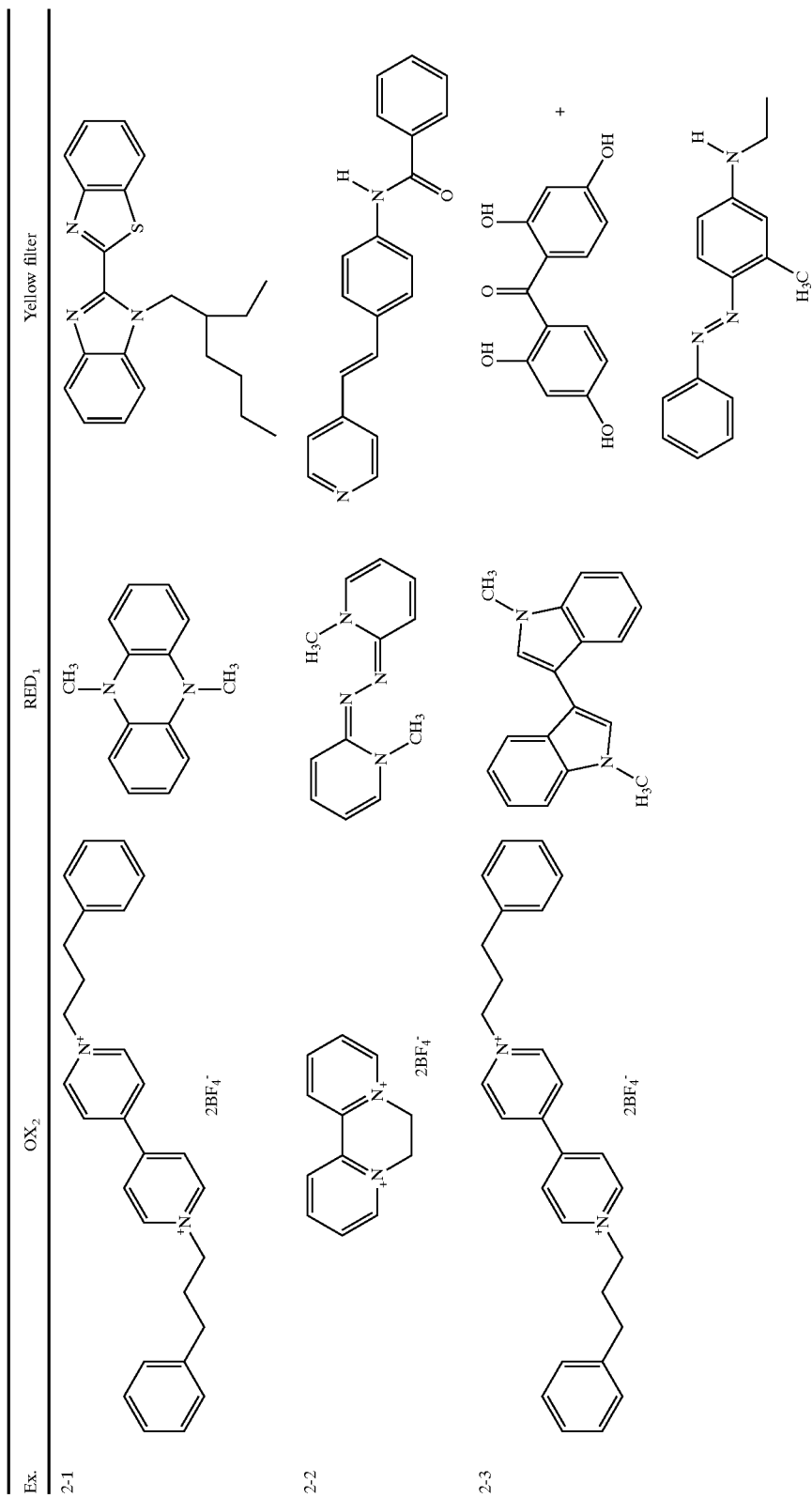

-continued
| Ex. | OX₂ | RED₁ | Yellow filter |
|---|---|---|---|
| 2-4 | 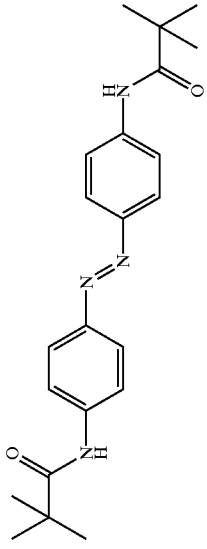 | 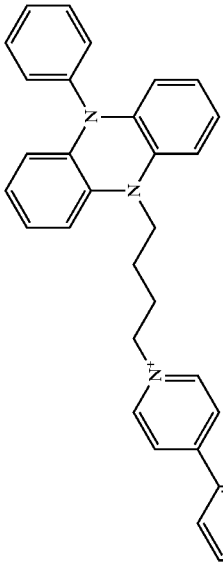 | 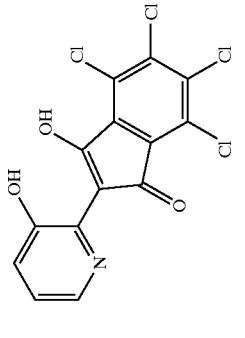 |
| 2-5 | 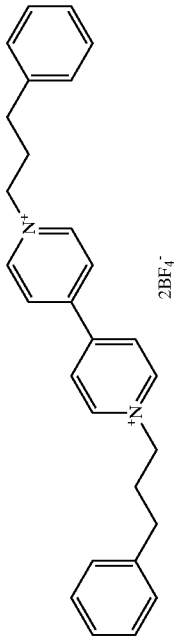 | 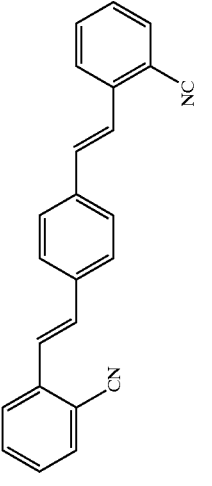 | 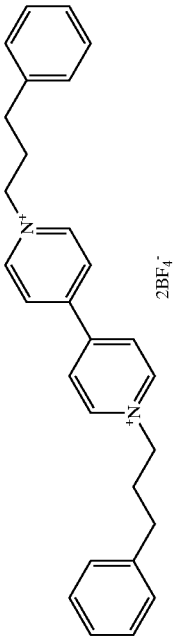 |
| 2-6 | | | |

| Ex. | OX₂ | RED₁ | Yellow filter |
|---|---|---|---|
| 2-7 | | | |
| 2-8 | | ferrocene | |
| 2-9 | | | |

| Ex. | OX$_2$ | RED$_1$ | Yellow filter |
|---|---|---|---|
| 2-10 | | | |
| 2-11 | | | |

2-12: A cell was constructed, filled and sealed as described in Example 2. However, use was made of two class plates which had been coated with ITO on one side and had been coated as follows on the other side: a 2% strength by weight solution of the polymeric yellow filter of the formula

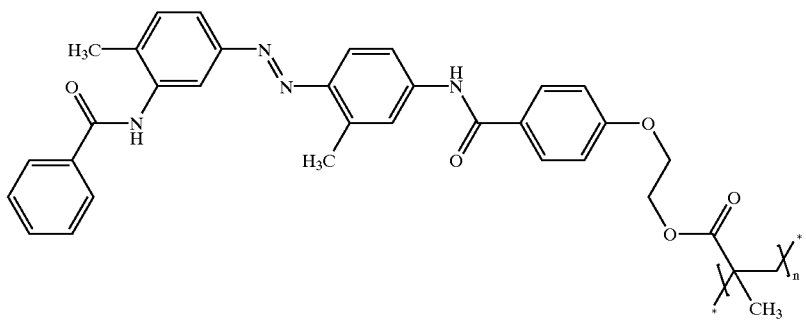

(CCCXXII)

in tetrahydrofuran was applied to the side of the plates which was not coated with ITO and dried overnight at 100° C. so as to give a dry film thickness of 1 μm.

Example 3

As in Example 1, use was made of two plates which had been coated with ITO on one side. On the other side, a PU coating composition comprising Desmodur and Desmophen (Bayer AG) and containing 3 per cent by weight of nanosize ZnO particles and 1 per cent by weight of the yellow filter of the formula (CCCXXI) (see Example 2) was applied in a wet film thickness of 240 μm by doctor blade coating. The films were dried overnight at 130° C.

A cell was constructed from these plates using a method analogous to Example 1.

The cell was filled with a solution which was 0.02 molar in the electrochromic compound of the formula (CCC) (see Example 1) in anhydrous, oxygen-free propylene carbonate. The cell was sealed as described in Example 1.

Example 3a (Comparison)

A cell was constructed as in Example 3, but use was made of glass plates which had been coated only with ITO.

Light Stability Test

The light stability of the cells from Examples 3 (according to the invention) and 3a was tested as described above, under the same test conditions. The cell of Example 3 had a better light stability than the cell of Example 3a.

Example 4

As in Example 1, use was made of two plates which had been coated with ITO on one side. They were provided on the other side with a layer containing nanosize $CeO_2$ particles. The layer was applied as follows. Firstly, a 6% strength by weight vinyl alcohol solution in water and a 7% strength by weight $CeO_2$ dispersion in water were made up. The nanosize $CeO_2$ particles were procured from Rhodia, Frankfurt, and have a size distribution of 8±2 nm. These solutions were mixed in a ratio of 1:1. This mixture is a 4% strength by weight polyvinyl alcohol solution containing 20% by weight of $CeO_2$, based on the total solids content.

The wet layer applied had a thickness of about 2 mm. The dry layer obtained after drying overnight at room temperature had a thickness of about 80 μm.

A cell was constructed from these plates using a method analogous to Example 1.

The cell was filled with a solution which was 0.02 molar in the electrochromic compound of the formula

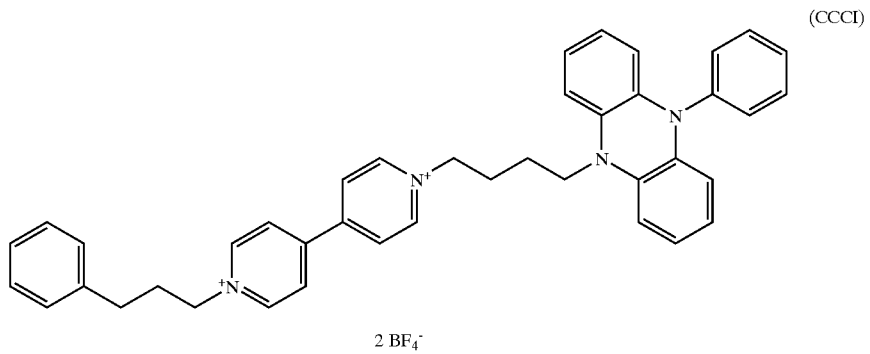

(CCCI)

2 $BF_4^-$ in anhydrous, oxygen-free propylene carbonate. The cell was sealed as described in Example 1.

Example 4a (Comparison)

A cell was constructed as in Example 4, but use was made of glass plates which had been coated only with ITO.

Light Stability Test

The light stability of the cells from Examples 4 (according to the invention) and 4a was tested as described above, under the same test conditions.

Comparison with the cells without a yellow filter shows a great increase in the stability.

| In % | 0 h | 0.5 h | 1.5 h | 3.5 h | 7.5 h | 15.5 h | 39.5 h | 87.5 h | 183.5 h |
|---|---|---|---|---|---|---|---|---|---|
| Cell with filter | 100 | 100 | 100 | 100 | 97 | 96 | 88 | 81 | 49 |
| Cell without filter | 100 | 68 | 49 | 40 | 32 | — | — | — | — |

Damage to the cell (20% less electrochromic swing) was found after 78 hours. Compared with the unprotected state, this corresponds to an improvement by a factor of 250.

Example 5

An electrochromic cell was constructed as described in Example 1.

The cell was filled with a solution which was 0.02 molar in the electrochromic compound of the formula (CCC) (see Example 1) and contained 5% by weight of the yellow filter of the formula (CCCXXI) (see Example 2) in anhydrous, oxygen-free propylene carbonate.

The cell was sealed as described in Example 1.

Example 5a (Comparison)

A cell was constructed as described in Example 5, but without the yellow filter of the formula (CCCXXI).

Light Stability Test

The light stability of the cells from Examples 5 (according to the invention) and 5a was tested as described above, under the same test conditions. The cell of Example 5 had a better light stability than the cell of Example 5a.

What is claimed is:

1. A light-stabilized electrochromic device comprising:
   (a) a pair of glass or plastic plates or plastic films wherein at least one such plate or film is provided on one side each with an electrically conductive coating, wherein
      (1) at least one such plate or film and its conductive coating is transparent,
      (2) one such plate or film and its conductive coating is optionally mirrored, and
      (3) the electrically conductive layer of one or both of the two plates or films is optionally divided into separate, individually contacted area segments;
   (b) a sealing ring joining the plates or films via the sides of their conductive coating wherein the volume formed by the two plates or films and the sealing ring is filled with an electrochromic medium; and
   (c) a yellow filter for which the wavelength at which the absorbance in the long-wavelength flank reaches half of the longest wavelength maximum absorbance is in the range of from 370 to 500 nm.

2. A light-stabilized electrochromic device according to claim 1, wherein the yellow filter is present in the electrochromic medium.

3. A light-stabilized electrochromic device according to claim 1, wherein the yellow filter is present in and/or on at least one of the two plates or films.

4. A light-stabilized electrochromic device according to claim 1 wherein the yellow filter is at least one substance and/or at least one material that absorbs in the wavelength range from 355 to 450 nm.

5. A light-stabilized electrochromic device according to claim 1, wherein the yellow filter comprises organic compound having at least one absorption maximum in the wavelength range from 355 to 430 nm.

6. A light-stabilized electrochromic device according to claim 5 wherein the organic compound has a width at half height of the absorption band having the absorption maximum in the wavelength range from 355 to 430 nm of less than 100 nm.

7. A light-stabilized electrochromic device according to claim 1 wherein the yellow filter comprises special glasses or oxidic or ceramic coatings.

8. A light-stabilized electrochromic device according to claim 1 wherein the yellow filter comprises nanosize particles.

9. A light-stabilized electrochromic device according to claim 1 additionally comprising a UV-absorbing material that protects the UV bands of the yellow filter.

10. A light-stabilized electrochromic device according to claim 9 wherein the UV-absorbing material comprises inorganic nanosize particles.

11. A light-stabilized electrochromic device according to claim 1 wherein the electrochromic medium contains at least one compound $OX_2$ of the formulas

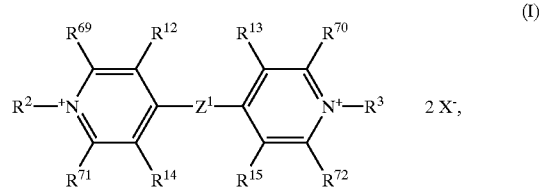

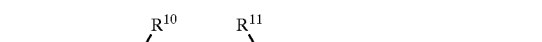

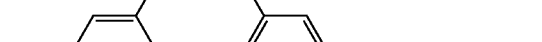

wherein

R², R³, R⁸ and R⁹ are, independently of one another, methyl, ethyl, propyl, butyl, benzyl, phenethyl, phenylpropyl, phenyl, 2-methylphenyl, or 2,6-dimethylphenyl or R⁸ and R⁹ together form a —(CH₂)₂— or —(CH₂)₃— bridge, R¹⁰ to R¹⁵ are hydrogen R⁶⁹ to R⁷³, R⁸⁰ and R⁸¹ are, independently of one another, hydrogen or methyl or R¹² and R⁶⁹ together, R¹³ and R⁷⁰ together, R⁷³ and R⁸⁰ together, and/or R⁷⁴ and R⁸¹ together form a —CH═CH—CH═CH— bridge, Z¹ is a direct bond or —CH═CH—, X⁻ is an anion that is redox-inert under the conditions, and at least one compound RED₁ of the formulas

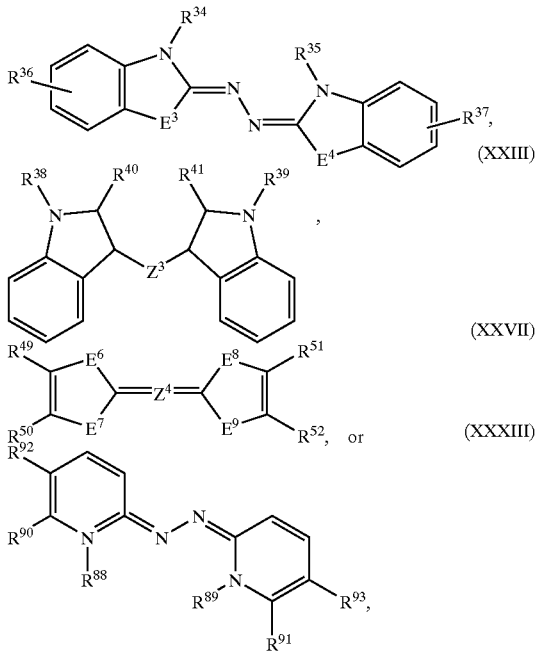

(XXII)

(XXIII)

(XXVII)

(XXXIII)

where

R³⁴, R³⁵, R³⁸, R³⁹, R⁸⁸ and R⁸⁹ are, independently of one another, methyl, ethyl, propyl, butyl, benzyl, phenethyl, phenylpropyl, or phenyl, R³⁶ and R³⁷ are hydrogen, Z³ is a direct bond or a —CH═CH— bridge, X⁴ is a direct double bond, R⁴⁰ and R⁴¹ are identical and are hydrogen or methyl, E³ and E⁴ are identical and are S, N—R⁵⁹, or C(CH₃)₂, E⁶ to E⁹ are identical and are S, R⁴⁹ to R⁵² are, independently of one another, hydrogen, methyl, cyano, or methoxycarbonyl or R⁴⁹ and R⁵⁰ together and/or R⁵¹ and R⁵² together form a —CH═CH—CH═CH— bridge, R⁹⁰ to R⁹³ are hydrogen or R⁹⁰ and R⁹² together and/or R⁹¹ and R⁹³ together form a —CH═CH—CH═CH— bridge, and R⁵⁹ is methyl, ethyl, propyl or butyl, where OX₂ and RED₁ are optionally linked via a bridge B according to the formula

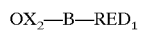

OX₂—B—RED₁ (La), where

B is —(CH₂)ₙ— and n is an integer from 3 to 6.

12. A window, partition, visor, glazing, or skylight comprising a light-stabilized electrochromic device according to claim 1.

13. Electrochromic substances of the formula (LX)

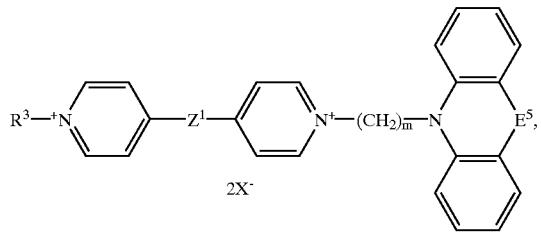

where

R³ is —(CH₂)₃—C₆H₅ or —(CH₂)₄—C₆H₅,

Z¹ is a direct bond,

E⁵ is N—C₆H₅, N—(CH₂)₃—C₆H₅ or N—(CH₂)₄—C₆H₅, m is an integer from 3 to 5 and

X⁻ is an anion which is redox-inert under the conditions.

14. Electrochromic substance of the formula

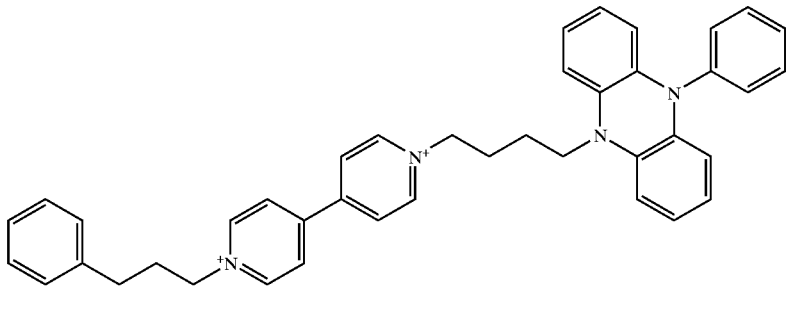

2 BF₄⁻.

* * * * *